(12) United States Patent
Hayakawa

(10) Patent No.: US 10,918,401 B2
(45) Date of Patent: Feb. 16, 2021

(54) MEDICAL DEVICE, MEDICAL SYSTEM, AND TREATMENT METHOD

(71) Applicant: TERUMO KABUSHIKI KAISHA, Tokyo (JP)

(72) Inventor: Koichi Hayakawa, Tokyo (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 211 days.

(21) Appl. No.: 15/914,418

(22) Filed: Mar. 7, 2018

(65) Prior Publication Data

US 2018/0256179 A1 Sep. 13, 2018

(30) Foreign Application Priority Data

Mar. 7, 2017 (JP) ................................. 2017-042882

(51) Int. Cl.
*A61B 17/22* (2006.01)
*A61B 17/221* (2006.01)
(Continued)

(52) U.S. Cl.
CPC ...... *A61B 17/22031* (2013.01); *A61B 17/221* (2013.01); *A61B 17/320758* (2013.01);
(Continued)

(58) Field of Classification Search
CPC ............ A61B 17/22031; A61B 17/221; A61B 17/320758
See application file for complete search history.

(56) References Cited

U.S. PATENT DOCUMENTS 5,011,488 A * 4/1991 Ginsburg ............... A61B 17/22
604/104
5,092,839 A * 3/1992 Kipperman ......... A61M 25/104
128/898
(Continued)

FOREIGN PATENT DOCUMENTS

JP S63-305857 A 12/1988
JP 2011-507602 A 3/2011
(Continued)

OTHER PUBLICATIONS

Office Action (Notice of Reasons for Refusal) dated Nov. 2, 2020, by the Japanese Patent Office in corresponding Japanese Patent Application No. 2017-042882 and an English Translation of the Office Action. (22 pages).

*Primary Examiner* — Richard G Louis
(74) *Attorney, Agent, or Firm* — Buchanan Ingersoll & Rooney PC

(57) ABSTRACT

A medical device, a medical system, and a treatment method are disclosed, which are capable of effectively crushing an object in a body lumen. The medical device can be used after being inserted into a capturing device capturing thrombi in a blood vessel and removing the thrombi to the outside of a body has at least two elongated shaft portions spaced apart from each other side by side and a cutting unit extending to a distal side from distal portions of at least two shaft portions, the cutting unit has linear portions inclined with respect to the shaft portions and a distal continuous portion extending to the distal side from distal portions of at least two linear portions, and at least the linear portions have sharp cutting blades.

19 Claims, 16 Drawing Sheets

(51) Int. Cl.
*A61B 17/3207* (2006.01)
*A61B 17/00* (2006.01)

(52) U.S. Cl.
CPC .............. *A61B 17/22032* (2013.01); *A61B 2017/00398* (2013.01); *A61B 2017/00477* (2013.01); *A61B 2017/00862* (2013.01); *A61B 2017/00867* (2013.01); *A61B 2017/2215* (2013.01); *A61B 2017/22067* (2013.01); *A61B 2017/22071* (2013.01); *A61B 2017/22079* (2013.01); *A61B 2017/22084* (2013.01); *A61B 2017/320775* (2013.01)

(56) References Cited

U.S. PATENT DOCUMENTS

| | | | | |
|---|---|---|---|---|
| 5,171,233 | A * | 12/1992 | Amplatz | A61B 17/221 604/540 |
| 5,908,435 | A * | 6/1999 | Samuels | A61B 17/22031 606/127 |
| 6,015,415 | A * | 1/2000 | Avellanet | A61B 18/14 606/110 |
| 2002/0065507 | A1* | 5/2002 | Zadno-Azizi | A61B 17/12022 604/509 |
| 2003/0163129 | A1* | 8/2003 | Lee | A61B 8/0825 606/47 |
| 2004/0199200 | A1* | 10/2004 | Teague | A61B 17/221 606/200 |
| 2009/0163846 | A1 | 6/2009 | Aklog et al. | |
| 2011/0213393 | A1 | 9/2011 | Aklog et al. | |
| 2013/0116715 | A1* | 5/2013 | Weber | A61B 17/320725 606/159 |
| 2015/0066045 | A1 | 3/2015 | Haack et al. | |
| 2015/0112376 | A1 | 4/2015 | Molaei et al. | |
| 2015/0157345 | A1* | 6/2015 | Haack | A61B 17/221 606/113 |
| 2017/0258488 | A1 | 9/2017 | Hatta et al. | |

FOREIGN PATENT DOCUMENTS

| | | |
|---|---|---|
| JP | 2016-530965 A | 10/2016 |
| WO | 2016/072107 A1 | 5/2016 |

* cited by examiner

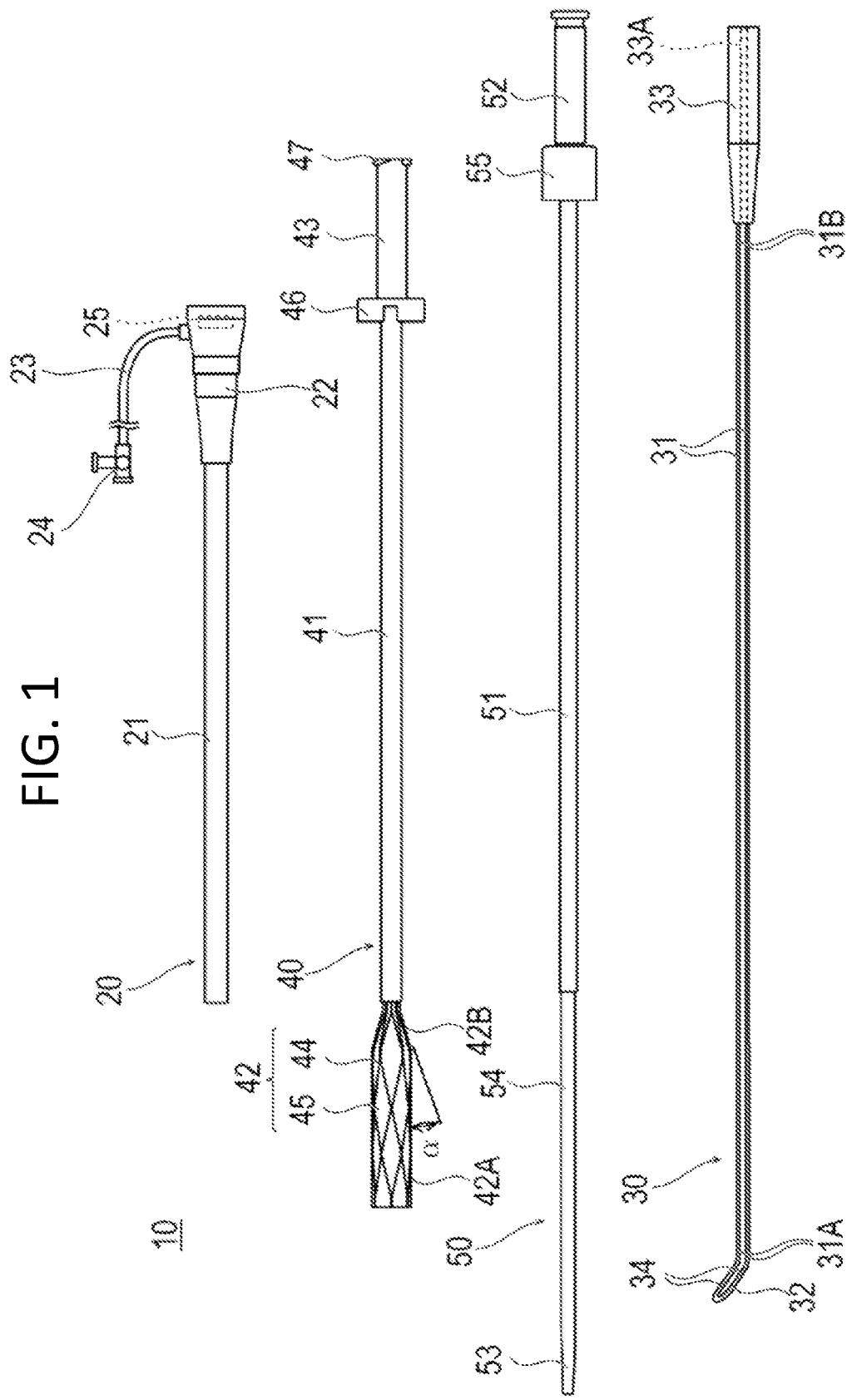

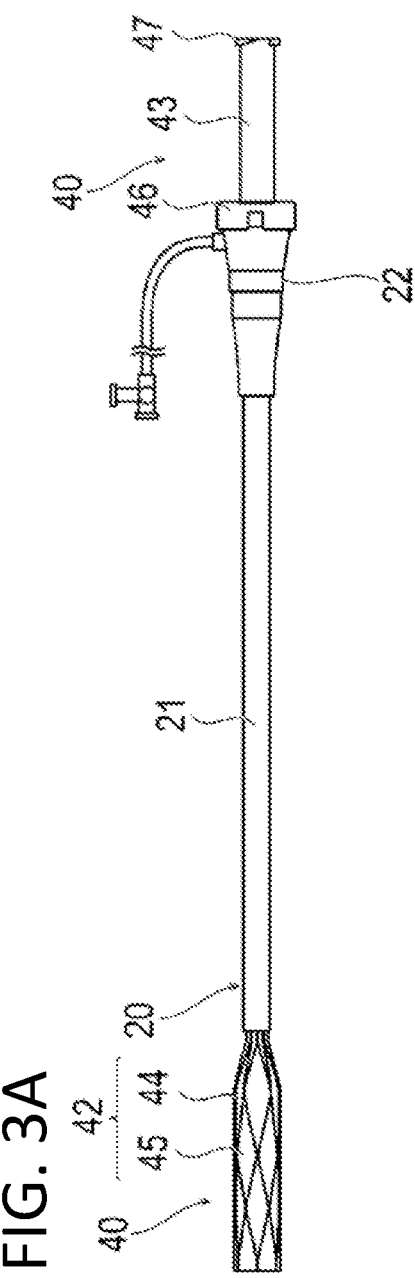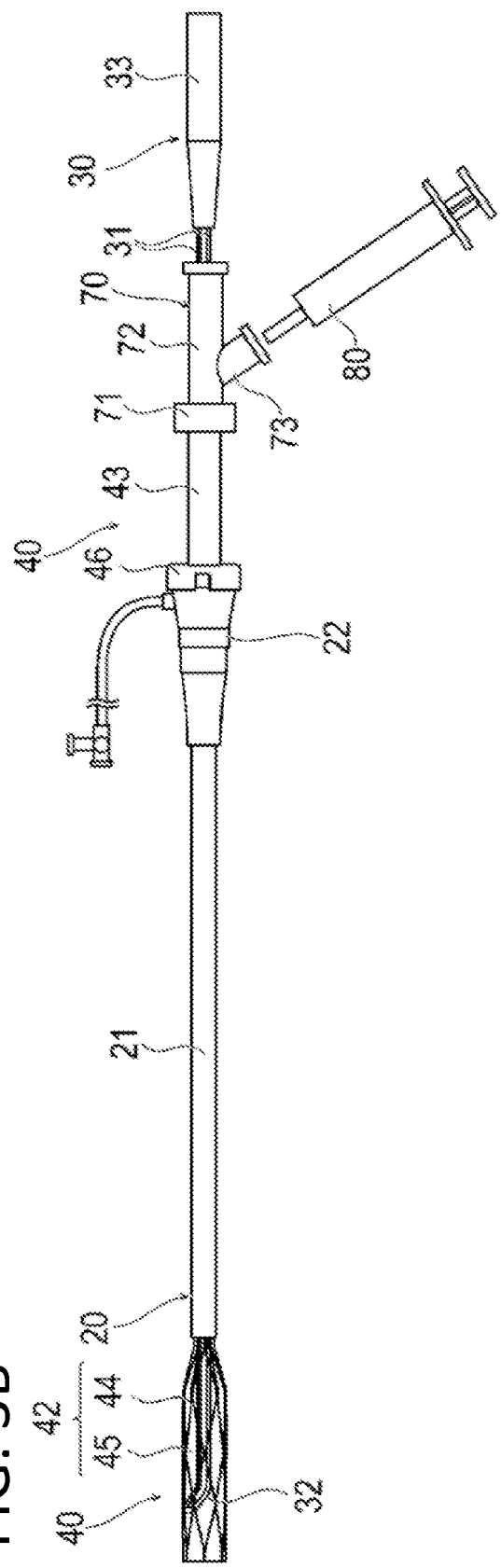

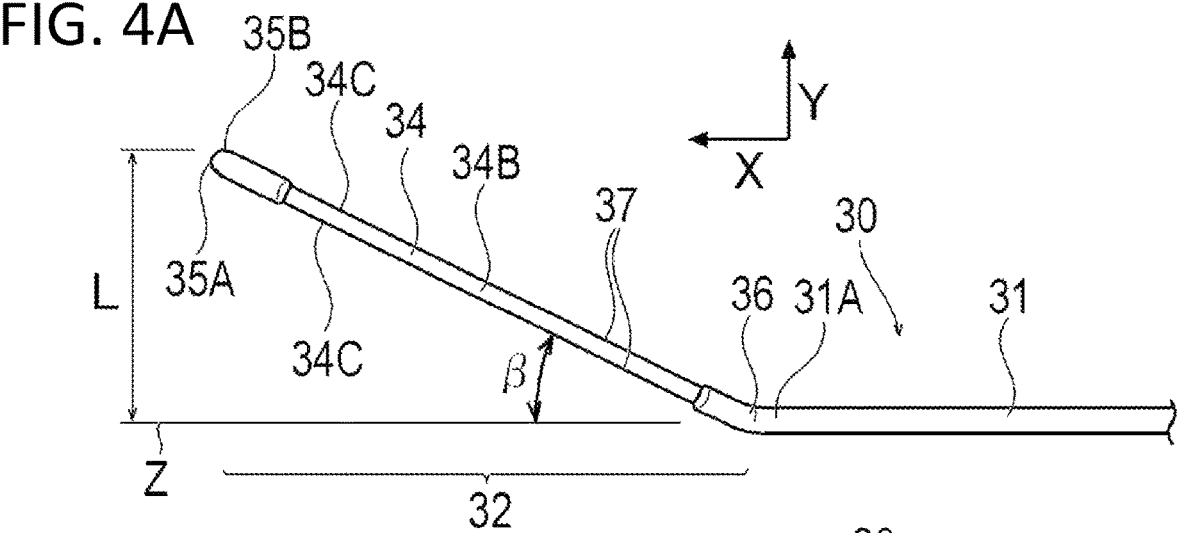
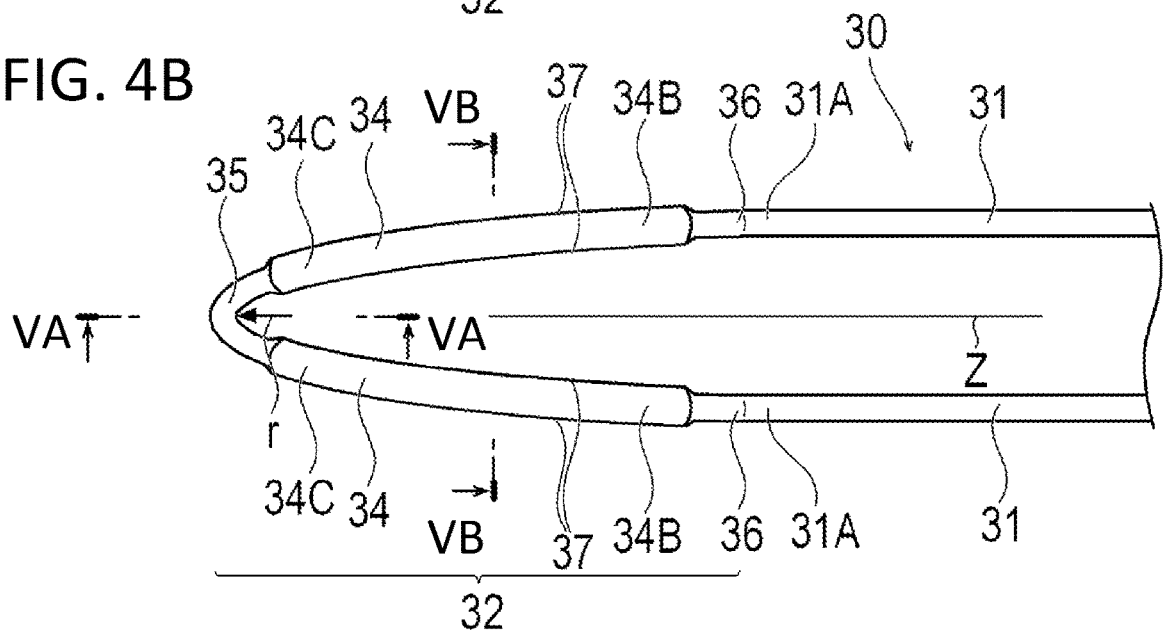

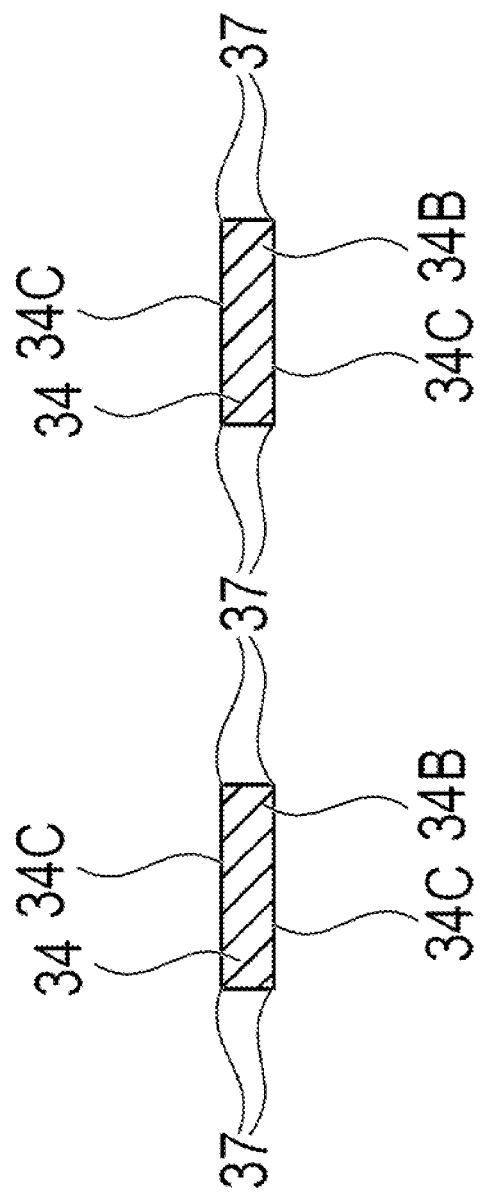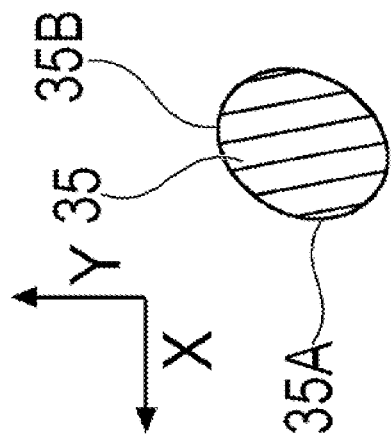

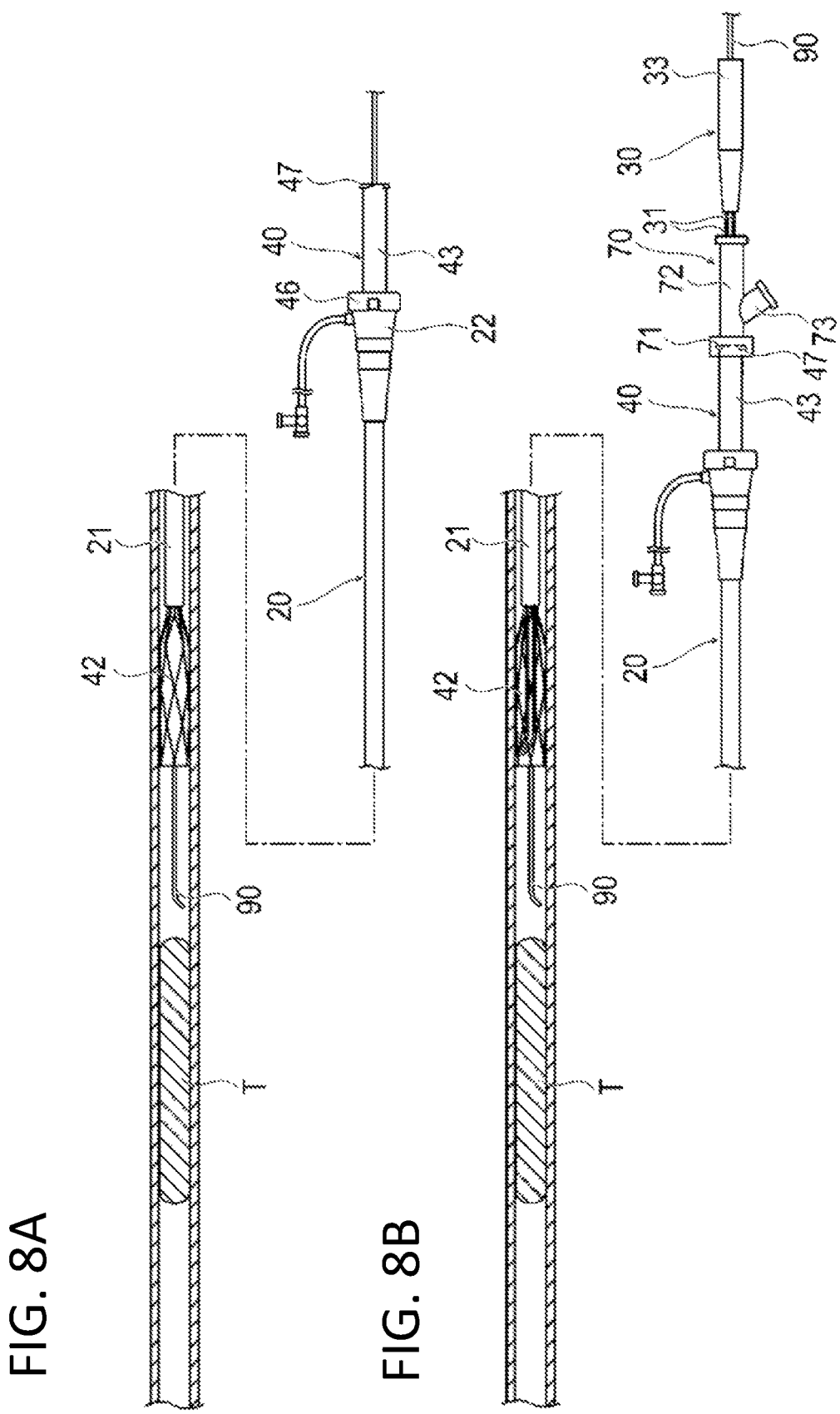

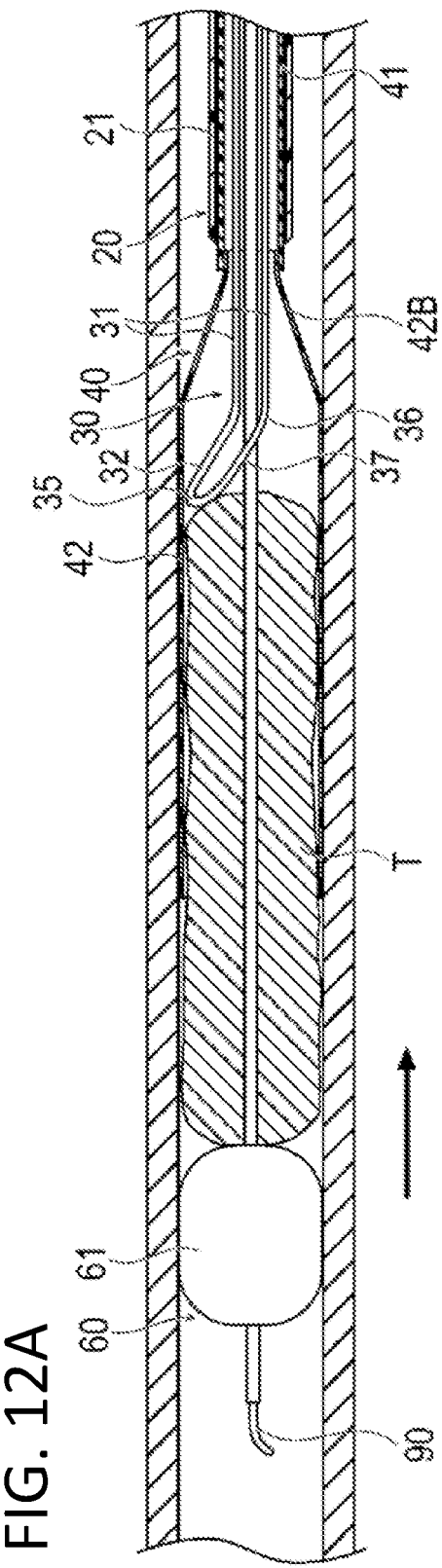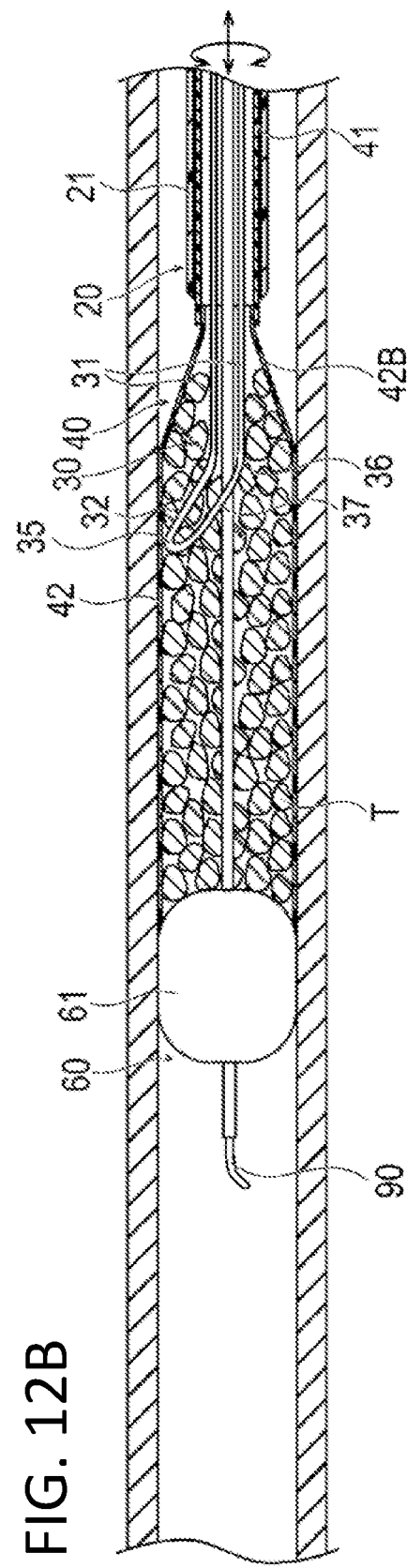

MEDICAL DEVICE, MEDICAL SYSTEM, AND TREATMENT METHOD

CROSS-REFERENCES TO RELATED APPLICATIONS

This application claims priority to Japanese Application No. 2017-042882 filed on Mar. 7, 2017, the entire content of which is incorporated herein by reference.

TECHNICAL FIELD

The present disclosure relates to a medical device, a medical system, and a treatment method for removing thrombi in a blood vessel.

BACKGROUND ART

Acute limb ischemia (ALI) occurs when thrombi formed in the heart, the aortic wall, or the like are released and obstruct the peripheral limb artery. Catheter-directed thrombolysis (CDT), percutaneous mechanical thrombectomy (PMT), and percutaneous aspiration thrombectomy (PAT) are known methods for the treatment of acute limb ischemia. However, thrombi cannot be easily removed by a percutaneous method based on blood vessel puncturing from the skin where the thrombi have a large dimension or where the thrombi are relatively hard. Accordingly, where the thrombi have a large dimension or where the thrombi are relatively hard, thrombectomy based on a catheter that has a balloon such as a Fogarty® catheter can be effective. In this method, the skin is surgically incised and the femoral artery is exposed. Next, the femoral artery is incised, the catheter is inserted into the blood vessel, and then the balloon is dilated after the catheter passes through the part obstructed by thrombi (or a stenosed part). Subsequently, the thrombi are moved up to the incised part of the blood vessel by the balloon being pulled to the proximal side, and then the thrombi are removed to the outside of the body from the incised part. This method, however, requires a surgical technique, and thus is dependent upon a doctor's technical skill. Accordingly, a patient's physical burden increases and the risk of post-treatment infection can be high.

Therefore, a method for removing thrombi by inserting a thrombus removal device that has a balloon into a blood vessel without incising the skin is disclosed in, for example, U.S. Patent Publication No. 2011/0213393. By this method, thrombi are pulled by the balloon of the thrombus removal device and accommodated in a funnel-shaped pipe body dilated in the blood vessel. Then, the thrombi are aspirated from the proximal side and the thrombi in the funnel-shaped pipe body are discharged to the outside of the body.

SUMMARY OF THE INVENTION

In a case where thrombi have a relatively large dimension or a case where thrombi are hard, the thrombi cannot be removed to the outside of the body with ease by the method disclosed in U.S. Patent Publication No. 2011/0213393 because the method is to remove thrombi by aspiration. In other words, it can be difficult to remove the thrombi in the funnel-shaped pipe body to the outside of the body via a thin sheath by an aspirating force alone.

In accordance with an exemplary embodiment, the present disclosure provides a medical device, a medical system, and a treatment method allowing an object in a body lumen to be effectively crushed such that the object can be easily removed to the outside of a body.

In accordance with an exemplary embodiment, a medical device is disclosed, which can be used after being inserted into a capturing device capturing an object in a body lumen and removing the object to an outside of a body, the medical device including at least two elongated shaft portions spaced apart from each other side by side and extending toward a distal side and a cutting unit extending to the distal side from distal portions of at least two shaft portions, in which the cutting unit has at least two linear portions inclined with respect to the shaft portions and a distal continuous portion extending to the distal side from distal portions of at least two linear portions and at least the linear portions have sharp cutting blades.

In accordance with an exemplary embodiment, a medical system is disclosed, which can be inserted into a body lumen to capture an object in the body lumen and remove the object to an outside of a body, the medical system including a capturing device for capturing the object in the body lumen and a medical device inserted into the capturing device to crush the object captured by the capturing device, in which the medical device includes at least two elongated shaft portions spaced apart from each other side by side and extending toward a distal side and a cutting unit extending to the distal side from distal portions of at least two shaft portions, the cutting unit has at least two linear portions inclined with respect to the shaft portions and a distal continuous portion extending to the distal side from distal portions of at least two linear portions, at least the linear portions have sharp cutting blades, the capturing device has a tubular sheath for capturing and a capturing portion that is a pipe body interlocked with a distal portion of the sheath for capturing and communicating with the sheath for capturing and is capable of dilating and deflating in a radial direction, and the cutting unit is capable of moving in an axial direction and a circumferential direction of the capturing portion inside the capturing portion.

In accordance with an exemplary embodiment, a treatment method is disclosed for capturing an object in a body lumen and removing the object to an outside of a body by using the medical system described above, the treatment method including a step of inserting the capturing device into the body lumen, a step of dilating the capturing portion in the body lumen, a step of inserting a distal portion of a removal device having a dilation portion capable of being dilated in a radial direction in a distal portion into the capturing device and allowing the dilation portion to reach a side closer to a distal side than the object in the body lumen, a step of moving the dilation portion to a proximal side by dilating the dilation portion and causing the object to be drawn into the capturing portion by the dilation portion, a step of crushing the object by moving the cutting unit inside the capturing portion, and a step of removing the crushed object to the outside of the body via the sheath for capturing.

In accordance with an exemplary embodiment, a treatment method is disclosed for capturing an object in a body lumen and removing the object to an outside of a body by using a removal device including a dilation portion configured to be dilated in a radial direction in a distal portion, a capturing device including a capturing portion and a sheath configured to remove the captured object in a tip portion configured to capture the object in the body lumen, and a cutting device including a cutting unit configured to crush the object captured by the capturing device, the treatment method comprising the steps of: inserting the capturing device into the body lumen; dilating the capturing portion in the body lumen; inserting the distal portion of the removal device into the capturing device and allowing the dilation portion to reach a side closer to a distal side than the object in the body lumen; moving the dilation portion to a proximal side by dilating the dilation portion and causing the object to be drawn into the capturing portion by the dilation portion; crushing the object by moving the cutting unit inside the capturing portion; and removing the crushed object to the outside of the body via the sheath for capturing According to the medical device, the medical system, and the treatment method configured as described above, the linear portion provided with the cutting blade is inclined with respect to the shaft portion, and thus the object can be effectively crushed by a movement in the capturing device into which the object is drawn in the body lumen. Accordingly, the medical device is capable of effectively crushing the object inside the capturing device such that the object can be easily removed to the outside of the body.

BRIEF DESCRIPTION OF THE DRAWINGS

FIG. 1 is a plan view illustrating a medical system according to an embodiment.

FIGS. 2A and 2B are plan views illustrating a state where a capturing device and an inner sheath are combined with an outer sheath, wherein FIG. 2A shows a state where a capturing portion of the capturing device is yet to be dilated, and FIG. 2B shows a state where the capturing portion of the capturing device is dilated.

FIGS. 3A and 3B are plan views illustrating a state where the capturing device is accommodated in the outer sheath, wherein FIG. 3A shows a state where the inner sheath is extracted from the capturing device, and FIG. 3B shows a state where a medical device is inserted into an outer sheath hub.

FIGS. 4A and 4B are diagrams illustrating a distal portion of the medical device, wherein FIG. 4A is a side view, and FIG. 4B is a top view.

FIG. 5A is a sectional view taken along line VA-VA of FIG. 4B, and FIG. 5B is a sectional view taken along line VB-VB of FIG. 4B.

FIGS. 6A and 6B are sectional views illustrating a distal portion of the medical system, wherein FIG. 6A shows a state where the capturing portion and the inner sheath are accommodated in the outer sheath, and FIG. 6B shows a state where the dilated capturing portion is inserted into the medical device.

FIGS. 7A and 7B are partial sectional views for showing a treatment using the medical system, wherein FIG. 7A shows a state where the medical system is inserted into a blood vessel, and FIG. 7B shows a state where the capturing portion is dilated in the blood vessel.

FIGS. 8A and 8B are partial sectional views for showing the treatment using the medical system, wherein FIG. 8A shows a state where the inner sheath is extracted from the blood vessel, and FIG. 8B shows a state where the capturing portion is dilated in the blood vessel.

FIGS. 12A and 12B are sectional views illustrating the distal portion of the medical system inserted into a blood vessel, wherein FIG. 12A shows a state where thrombi are accommodated in the capturing portion, and FIG. 12B shows a state where thrombi inside the capturing portion are crushed by the medical device.

DESCRIPTION OF EMBODIMENTS

Figure 2A:
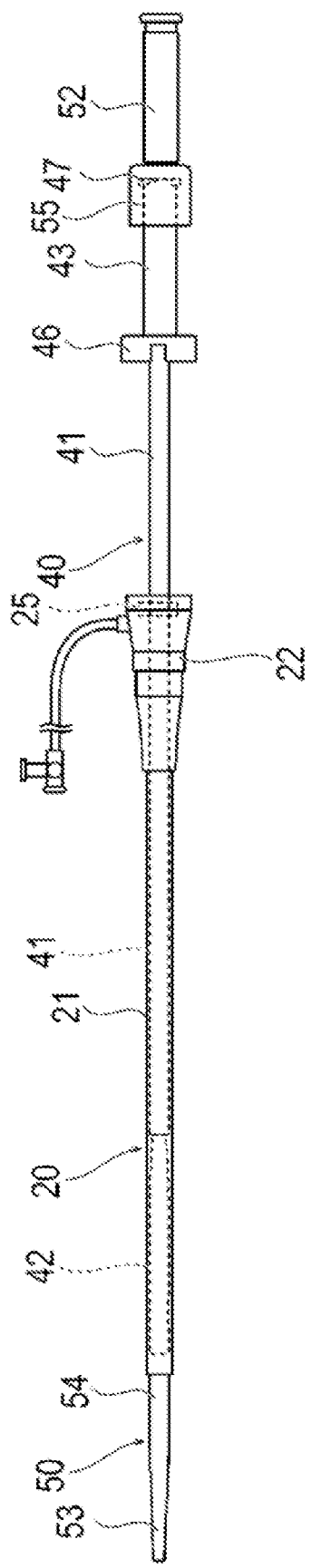

Hereinafter, an embodiment of the present invention will be described with reference to accompanying drawings. The dimension ratios in the respective drawings are exaggerated for convenience of description and differ from the actual ratios in some cases. In the present specification, the side of the device that is inserted into a blood vessel will be referred to as a "distal side" and the hand-side that is operated will be referred to as a "proximal side".

A medical system 10 according to the embodiment of the present disclosure can be used to capture intra-arterial thrombi and remove the thrombi to the outside of the body. In the present specification, the side of the device that is inserted into a blood vessel will be referred to as a "distal side" and the hand-side that is operated will be referred to as a "proximal side".

As illustrated in FIG. 1, the medical system 10 according to the present embodiment has an outer sheath 20, a medical device 30, a capturing device 40, and an inner sheath 50. The medical system 10 can be used with a known thrombus removal device 60 (refer to FIG. 9). The thrombus removal device 60 can be a Fogarty® catheter that has a balloon 61 for moving thrombi in a blood vessel.

The outer sheath 20 is a known introducer sheath. The outer sheath 20 has an outer sheath main body 21, an outer sheath hub 22 interlocking with the proximal portion of the outer sheath main body 21, a port portion 23 communicating with the outer sheath hub 22, and a valve body 25 inside the outer sheath hub 22.

The outer sheath main body 21 is a pipe body capable of accommodating the capturing device 40, the inner sheath 50, and the medical device 30. The outer diameter of the distal side end portion of the outer sheath main body 21 decreases in a tapered shape so that the insertion resistance into a blood vessel and injury to a vascular wall are reduced. The inner peripheral surface of the outer sheath main body 21 is in contact with the outer peripheral surface of a sheath 41 for capturing of the capturing device 40. In accordance with an exemplary embodiment, it can be desirable that the outer sheath main body 21 and the sheath 41 for capturing have a small step as a result.

In accordance with an exemplary embodiment, the outer sheath hub 22 is disposed in the proximal portion of the outer sheath main body 21 and communicates with the lumen of the outer sheath main body 21. The capturing device 40 passes through the outer sheath hub 22. The port portion 23 interlocks with the outer sheath hub 22 and communicates with the lumen of the outer sheath main body 21 via the lumen of the outer sheath hub 22. The port portion 23 has a three-way stopcock (valve) 24 in an end portion. By a syringe or the like being connected to the three-way stopcock 24, the lumen of the outer sheath main body 21 can be primed or a contrast agent or medicine can be injected into the outer sheath main body 21.

The valve body 25 is a member for sealing the lumens of the outer sheath hub 22 and the outer sheath main body 21. The valve body 25 can be flexibly deformed and is placed on the inner peripheral surface of the outer sheath hub 22. As illustrated in FIG. 2A, the valve body 25 is slidably in contact with the outer peripheral surface of the capturing device 40. In addition, the valve body 25 is capable of fixing the capturing device 40 and the outer sheath 20 by pressing the capturing device 40 by an elastic force in a state where the capturing device 40 is inserted. In accordance with an exemplary embodiment, even when fixed by the valve body 25, the capturing device 40 and the outer sheath 20 can be relatively moved in the axial direction by a force being exerted with the capturing device 40 and the outer sheath 20 grasped. The valve body 25 can be, for example, a member in which a break is made in the middle of a disk-shaped elastic body. The elastic body can be, for example, natural rubber, silicone rubber, or various elastomers. The valve body 25 inhibits air from entering a body and inhibits blood leakage via the outer sheath 20 while allowing insertion and removal of the capturing device 40.

The length of the outer sheath main body 21 is appropriately set and can be, for example, 80 mm to 800 mm. The outer diameter of the outer sheath main body 21 is appropriately set and can be, for example, 2.0 mm to 5.0 mm. The inner diameter of the outer sheath main body 21 is appropriately set and can be, for example, 1.5 mm to 4.5 mm.

Preferably, the constituent material of the outer sheath main body 21 is a flexible material, and suitably usable examples include polyolefin such as polyethylene and polypropylene, polyester such as polyamide and polyethylene terephthalate, fluoropolymer such as polytetrafluoroethylene (PTFE) and ethylene-tetrafluoroethylene copolymer (ETFE), polyether ether ketone (PEEK), and polyimide.

As illustrated in FIG. 1, the capturing device 40 is a device for capturing thrombi in a blood vessel. The capturing device 40 has the sheath 41 for capturing, a capturing portion 42, and a hub 43 for capturing.

The sheath 41 for capturing slidably accommodates the inner sheath 50 and the medical device 30. In addition, the lumen of the sheath 41 for capturing is used to transport crushed thrombi to the outside.

The capturing portion 42 is a tubular structure and the outer peripheral surface of the capturing portion 42 touches an intravascular wall when the capturing portion 42 dilates. The proximal side end portion of the capturing portion 42 interlocks with the distal side end portion of the sheath 41 for capturing. The lumen of the capturing portion 42 communicates with the lumen of the sheath 41 for capturing. The capturing portion 42 has a reticular elastic portion 44 that can be elastically deformed and a membrane body 45 that covers the outer peripheral surface of the elastic portion 44. The elastic portion 44 is a reticular tubular body that has a gap. The membrane body 45 blocks the gap of the reticular elastic portion 44. The membrane body 45 limits passage of thrombi through the gap of the elastic portion 44.

The elastic portion 44 and the membrane body 45 constitute the capturing portion 42, and the capturing portion 42 has a distal side capturing portion 42A positioned on the distal side and a proximal side capturing portion 42B positioned on the proximal side. The distal side capturing portion 42A is capable of coming into close contact with an intravascular wall by the dilating force of the elastic portion 44. The outer diameter of the distal side capturing portion 42A is larger than the outer diameter of the sheath 41 for capturing in a natural state where no external force acts. The inner diameter and the outer diameter of the distal side capturing portion 42A are almost constant along the axial direction. The inner diameter and the outer diameter of the proximal side capturing portion 42B decrease from the distal side capturing portion 42A toward the proximal side in a natural state.

Figure 2B:
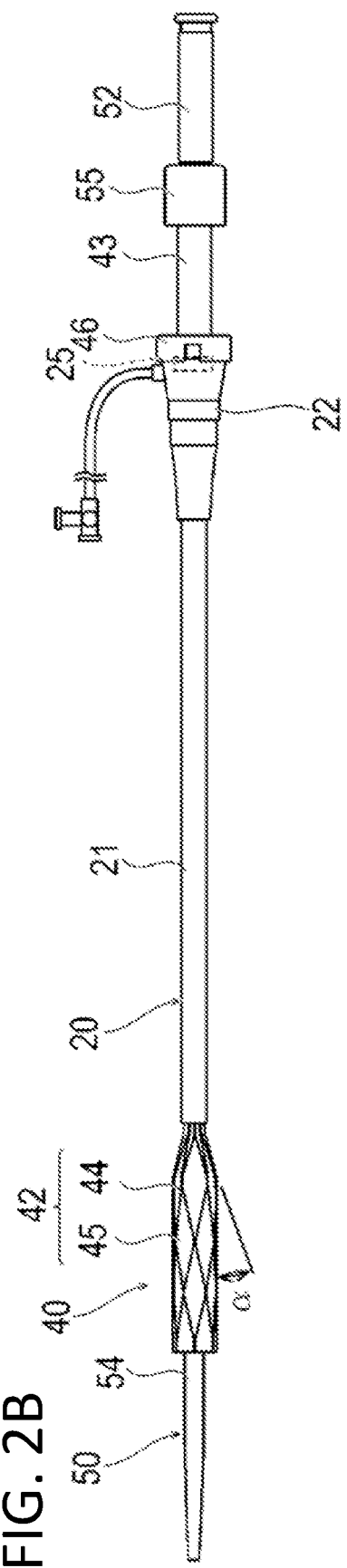
Figure 6A:
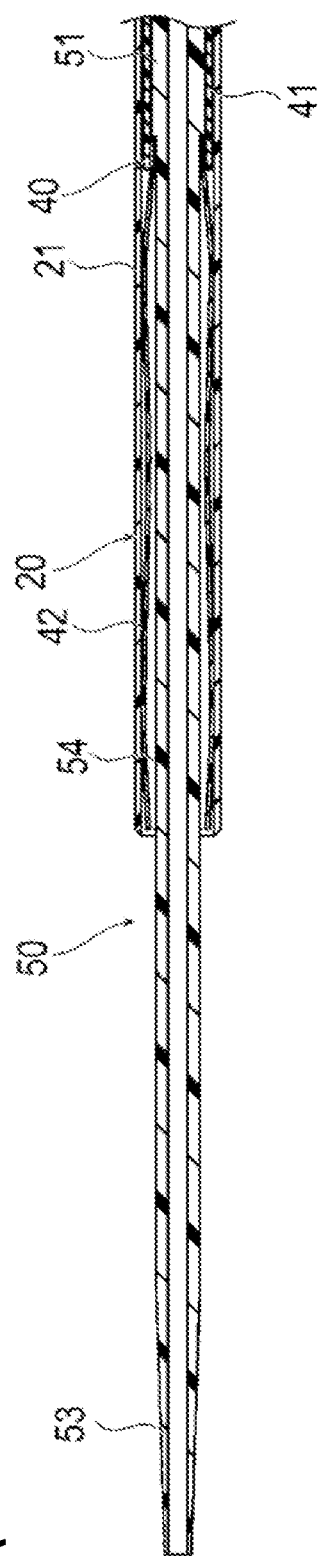
Figure 6B:
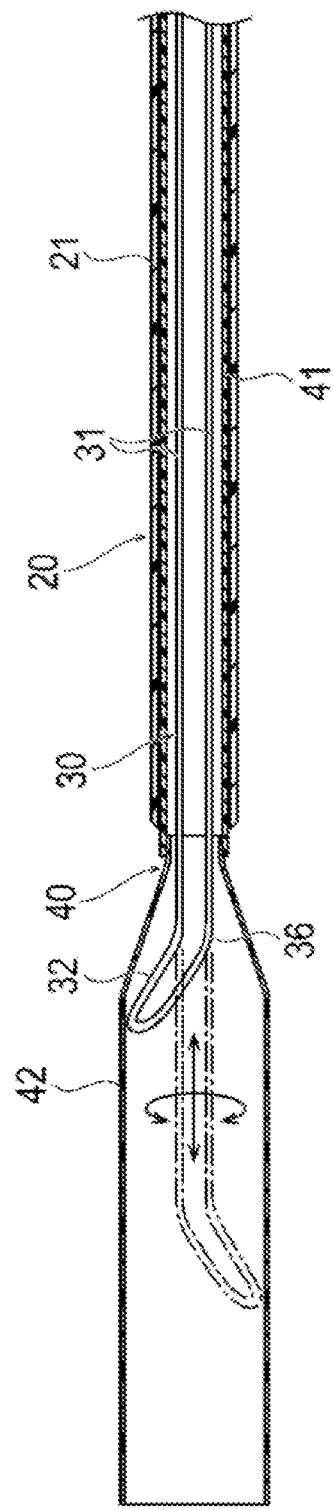

As illustrated in FIGS. 2A and 6A, the capturing portion 42 can be accommodated in the outer sheath 20 by elastically deflating in the radial direction. The capturing portion 42 dilates radially outward by the elastic force (restoring force) of the elastic portion 44 as illustrated in FIGS. 2B and 6B by going outside from the outer sheath 20.

As illustrated in FIG. 1, the hub 43 for capturing is disposed in the proximal portion of the sheath 41 for capturing and communicates with the lumen of the sheath 41 for capturing. The inner sheath 50 and the medical device 30 can be inserted into the hub 43 for capturing. A hub interlock portion 46 that is capable of interlocking with the outer sheath hub 22 is disposed in the distal portion of the hub 43 for capturing. A male connector 47 that is capable of interlocking with a female connector 55, which is disposed in an inner sheath hub 52 of the inner sheath 50, is disposed in the proximal portion of the hub 43 for capturing. When the hub interlock portion 46 interlocks with the outer sheath hub 22, the capturing portion 42 is put into a dilated state without being accommodated in the outer sheath 20 as illustrated in FIG. 2B. In addition, when the male connector 47 interlocks with the female connector 55, the distal side end portion of the inner sheath 50 is positioned to be closer to the distal side than the distal side end portion of the capturing device 40.

The length of the sheath 41 for capturing is appropriately set and can be, for example, 90 mm to 950 mm. The outer diameter of the sheath 41 for capturing is appropriately set and can be, for example, 1.4 mm to 4.4 mm. The inner diameter of the sheath 41 for capturing is appropriately set and can be, for example, 1.2 mm to 4.2 mm.

Preferably, the constituent material of the sheath 41 for capturing is a flexible material, and the material that can be applied to the outer sheath main body 21 described above can be applied.

The axial-direction length of the capturing portion 42 in a natural state is appropriately set and can be, for example, 10 mm to 100 mm. The maximum outer diameter of the capturing portion 42 in a natural state is appropriately set depending on the inner diameter of the applied blood vessel and can be, for example, 5 mm to 15 mm.

An inclination angle α that the proximal side capturing portion 42B has in a natural state with respect to the central axis is appropriately set. For example, the inclination angle α can be 15 degrees to 45 degrees. Preferably, the inclination angle α can be 20 degrees to 40 degrees. More preferably, the inclination angle α can be 25 degrees to 35 degrees.

Preferably, the constituent material of the elastic portion 44 is a flexible material, and suitably usable examples include a shape memory alloy to which a shape memory effect and superelasticity are given by heat treatment, stainless steel, tantalum (Ta), titanium (Ti), silver (Pt), gold (Au), tungsten (W), polyolefin such as polyethylene and polypropylene, polyester such as polyamide and polyethylene terephthalate, fluoropolymer such as tetrafluoroethylene-ethylene copolymer (ETFE), polyether ether ketone (PEEK), and polyimide. Preferably used as the shape memory alloy is a Ni—Ti alloy, a Cu—Al—Ni alloy, a Cu—Zn—Al alloy, or a combination thereof. Examples of structures in which a plurality of materials is combined include a structure in which a Pt-based core wire is coated with a Ni—Ti alloy for contrasting properties and a structure in which gold plating is performed on a Ni—Ti alloy-based core wire.

Preferably, the constituent material of the membrane body 45 is a flexible material, and suitably usable examples include polyurethane, natural rubber, silicone resin, and polyester elastomer. The membrane body 45 may also be a member that has air permeability and liquid permeability.

As illustrated in FIG. 1, the inner sheath 50 is a device for smoothly guiding the outer sheath 20 and the sheath 41 for capturing up to a target position of a blood vessel via a guide wire. The inner sheath 50 has an inner sheath main body 51 and the inner sheath hub 52.

The inner sheath main body 51 slidably accommodates the guide wire. A tapered portion 53 that has an outer diameter decreasing toward the distal side is formed in the distal portion of the inner sheath main body 51 for smooth insertion into a blood vessel. In addition, an outer surface containing unit 54 capable of accommodating the capturing portion 42 is formed on the outer peripheral surface of the distal portion of the inner sheath main body 51. In accordance with an exemplary embodiment, the outer surface containing unit 54 is smaller in outer diameter than the proximal portion of the inner sheath main body 51.

The inner sheath hub 52 is disposed in the proximal portion of the inner sheath main body 51 and communicates with the lumen of the inner sheath main body 51. A guide wire can be inserted into the inner sheath hub 52. The female connector 55 that is capable of interlocking with the male connector 47 of the hub 43 for capturing is disposed in the distal portion of the inner sheath hub 52. As illustrated in FIGS. 2A and 2B, the inner sheath 50 can be inserted into the lumen of the capturing device 40 from the hub 43 for capturing. In addition, the inner sheath 50 can be withdrawn from the hub 43 for capturing as illustrated in FIG. 3A.

The length of the inner sheath main body 51 is appropriately set and can be, for example, 110 mm to 1,000 mm. The outer diameter of the proximal portion of the inner sheath main body 51 is appropriately set and can be, for example, 1.1 mm to 4.1 mm. The outer diameter of the outer surface containing unit 54 is appropriately set and can be, for example, 1.0 mm to 4.0 mm. The inner diameter of the inner sheath main body 51 is appropriately set and can be, for example, 0.8 mm to 2.0 mm.

Preferably, the constituent material of the inner sheath main body 51 is a flexible material, and the material that can be applied to the outer sheath main body 21 described above can be applied.

As illustrated in FIGS. 1, 4A, 4B, 5A, and 5B, the medical device 30 is a device for finely crushing thrombi drawn into the capturing portion 42. The medical device 30 has two elongated shaft portions 31, a cutting unit 32 extending to the distal side from distal portions 31A of the shaft portions 31, and an operation unit 33. The two elongated shaft portions 31 are not limited to those made up of two wire rods and may also be made up of one wire rod. When configured by one wire rod being bent, the two shaft portions 31 extend substantially in parallel to each other side by side. The two shaft portions 31 and the cutting unit 32 are configured by one wire rod being bent. The two shaft portions 31 can be inserted into the lumen of the capturing device 40. The two shaft portions 31 are cylindrical wire rods that are spaced apart from each other side by side and extent substantially in parallel to each other. The cross-sectional shape of the shaft portion 31 is not limited to a circular shape.

The cutting unit 32 can be elastically deformed. In accordance with an exemplary embodiment, the cutting unit 32 can be integrally connected and continuous to the distal portions 31A of the two shaft portions 31. The cutting unit 32 has two linear portions 34 extending at an angle to the shaft portions 31 in a natural state and one distal continuous portion 35 continuous from the distal side end portions of the two linear portions 34. The distal continuous portion 35 is integrally connected and continuous to the two linear portions 34. The distal continuous portion 35 may also be continuous by being interlocked with and connected to the two linear portions 34 that are separate bodies. The two linear portions 34 are curved to become closer to each other toward the distal side. The linear portion 34 has a bent portion 36 bent with respect to the central axis of the shaft portion 31 and a cutting blade 37 positioned to be closer to the distal side than the bent portion 36. The bending directions of the bent portions 36 of the two linear portions 34 are substantially the same as each other. Preferably, in accordance with an exemplary embodiment, a bending angle β of the bent portion 36 with respect to the central axis of the shaft portion 31 is substantially equal to the inclination angle α of the proximal side capturing portion 42B in a natural state. The bending angle β of the bent portion 36 is appropriately set. For example, the bending angle β can be 15 degrees to 45 degrees. Preferably, the bending angle β can be 20 degrees to 40 degrees. More preferably, the bending angle β can be 25 degrees to 35 degrees. The bent portion 36 can be accommodated in the sheath 41 for capturing by being substantially linearly deformed. Preferably, a maximum distance L from a central axis of rotation Z of the shaft portion 31 to the site where the cutting unit 32 is farthest away in a separation direction Y is substantially equal to or larger to some extent than the maximum inner diameter of the dilated capturing portion 42. The central axis of rotation Z of the shaft portion 31 is a central axis in a case where all of the shaft portions 31 integrally rotate. The central axis of rotation Z of the shaft portion 31 is positioned in the middle of the two central axes that are positioned at the centers of the respective shaft portions 31.

The two linear portions 34 have two flat surfaces 34C that are parallel to each other in a cross section perpendicular to the extending direction. In other words, the two linear portions 34 have flat plate portions 34B provided with two flat surfaces 34C. The two flat plate portions 34B are parallel to each other and are positioned on the same plane. As a result, the two flat plate portions 34B are easily formed. In accordance with an exemplary embodiment, the two flat plate portions 34B may not be parallel to each other and may not be positioned on the same plane, either. The sharp cutting blade 37 is formed in the edge portion of the flat surface 34C. The angle of the cutting blade 37 in a cross section perpendicular to the extending direction of the linear portion 34 can be approximately 90 degrees. The angle of the cutting blade 37 may exceed 90 degrees to some extent or may be less than 90 degrees as well. Although the number of the cutting blades 37 in a cross section perpendicular to the extending direction of each linear portion 34 is four in the present embodiment, the number is not limited.

The distal continuous portion 35 is formed by a wire rod with a circular section being smoothly curved. Accordingly, the cross-sectional shape of the wire rod in the distal continuous portion 35 can have a circular shape, an elliptical shape, or a distorted circular shape. No cutting blade 37 is formed in the distal continuous portion 35. Accordingly, the outer surface of the distal continuous portion 35 can be smoothly formed by at least one of a flat surface and a curved surface and is provided with no sharp cutting blade. Therefore, damage to members (balloon 61 and capturing portion 42) coming into contact with the distal continuous portion 35 can be inhibited.

In accordance with an exemplary embodiment, no cutting blade is formed on a tip surface 35A of the distal continuous portion 35 on the distal direction X side and a side surface 35B on the separation direction Y side separated from the central axis of rotation Z of the shaft portion 31. In other words, the tip surface 35A and the side surface 35B can be smoothly formed by at least one of a flat surface and a curved surface. The tip surface 35A is a site that is likely to come into contact with the balloon 61 positioned on the distal direction X side. The side surface 35B is a site that is likely to come into contact with the inner peripheral surface of the capturing portion 42 on the separation direction Y side. Accordingly, damage to the balloon 61 and the capturing portion 42 can be inhibited. The cutting blade 37 can be easily formed by a wire rod being cut after collapsing into a flat plate shape. Methods for forming the cutting blade are not particularly limited. Therefore, the cutting blade that is a separate member may also be fixed to a wire rod.

The operation unit 33 is a tubular structure that is grasped and operated by an operator. A proximal portion 31B of the shaft portion 31 interlocks with the operation unit 33. The operation unit 33 is provided with a through-hole 33A communicating with the gap between the two shaft portions 31. The thrombus removal device 60 and a guide wire can be inserted into the through-hole 33A. Accordingly, the inner diameter of the through-hole 33A is equal to or larger than the outer diameter of the site of the thrombus removal device 60 that passes through the through-hole 33A. The operation unit 33 is insert-molded such that the proximal side end portion of the shaft portion 31 is embedded. Methods for forming the operation unit 33 are not particularly limited.

As illustrated in FIG. 3B, the cutting unit 32 is capable of reaching the inside of the capturing portion 42 once the medical device 30 is inserted into the capturing device 40 via a Y connector 70. In addition, it is preferable that the most distal portion of the cutting unit 32 is positioned close to the most distal portion of the capturing portion 42 and is positioned inside the capturing portion 42 in a state where the operation unit 33 is closest to the Y connector 70. Accordingly, the cutting unit 32 does not protrude to the distal side from the capturing portion 42 and does not hurt a biological tissue. The cutting unit 32 is capable of rotating in the circumferential direction of the capturing portion 42 inside the capturing portion 42 as illustrated in FIG. 6B by the operation unit 33 being operated. Furthermore, the cutting unit 32 is capable of moving in the axial direction of the capturing portion 42 inside the capturing portion 42.

The length of the shaft portion 31 is appropriately set and can be, for example, 100 mm to 1,000 mm. The diameter of the wire rod that constitutes the shaft portion 31 and the cutting unit 32 is appropriately set. For example, the diameter of the wire rod can be 0.2 mm to 0.7 mm. Preferably, the diameter of the wire rod can be 0.3 mm to 0.6 mm. More preferably, the diameter of the wire rod can be 0.4 mm to 0.5 mm. The two shaft portions 31 can be accommodated in the sheath 41 for capturing. In addition, it is preferable that the gap between the two shaft portions 31 is equal to or larger than the maximum outer diameter of the sheath and the balloon 61 of the thrombus removal device 60 such that the thrombus removal device 60 is capable of passing through the gap. As a result, the two shaft portions 31 are capable of rotating in the circumferential direction and are capable of moving in the axial direction in the gap between the inner peripheral surface of the sheath 41 for capturing and the outer peripheral surface of the thrombus removal device 60. In addition, the two shaft portions 31 do not occupy the gap between the inner peripheral surface of the sheath 41 for capturing and the outer peripheral surface of the thrombus removal device 60. Accordingly, thrombi can be discharged to the outside of the body without being inhibited by the medical device 30 by the gap between the inner peripheral surface of the sheath 41 for capturing and the outer peripheral surface of the thrombus removal device 60 being used. The gap between the two shaft portions 31 is appropriately set. For example, the gap between the two shaft portions 31 can be 0.8 mm to 4.0 mm. Preferably, the gap between the two shaft portions 31 can be 1.5 mm to 3.5 mm. More preferably, the gap between the two shaft portions 31 can be 2.0 mm to 3.0 mm. Preferably, a curvature r of the distal continuous portion 35 is almost equal to the inner diameter of the sheath 41 for capturing. As a result, the distal continuous portion 35 can be moved inside the sheath 41 for capturing. The curvature r of the distal continuous portion 35 is appropriately set. For example, the curvature r of the distal continuous portion 35 can be 0.4 mm to 2.0 mm. Preferably, the curvature r of the distal continuous portion 35 can be 0.75 mm to 1.75 mm. More preferably, the curvature r of the distal continuous portion 35 can be 1.0 mm to 1.5 mm.

Preferably, the constituent material of the shaft portion 31 and the cutting unit 32 is a material that has a certain degree of strength, and suitably usable examples include a shape memory alloy to which a shape memory effect and superelasticity are given by heat treatment, stainless steel, tantalum (Ta), titanium (Ti), silver (Pt), gold (Au), tungsten (W), polyolefin such as polyethylene and polypropylene, polyester such as polyamide and polyethylene terephthalate, fluoropolymer such as tetrafluoroethylene-ethylene copolymer (ETFE), polyether ether ketone (PEEK), and polyimide.

As illustrated in FIG. 3B, the Y connector 70 can be a known Y connector and is provided with an interlock portion 71 that is a female connector which is capable of interlocking with the hub 43 for capturing, a tubular main body portion 72, and a side pipe 73 branching from the main body portion 72. A valve body (not illustrated) is placed inside the main body portion 72. A syringe 80 can be interlocked with the side pipe 73. The syringe 80 is used for injection of a thrombolytic agent, a contrast agent, or the like and aspiration of thrombi.

Described below is a method for capturing and removing thrombi T (refer to FIG. 10) obstructing an artery more peripheral than an iliac artery by using the medical system 10 according to the present embodiment.

Figure 7A:
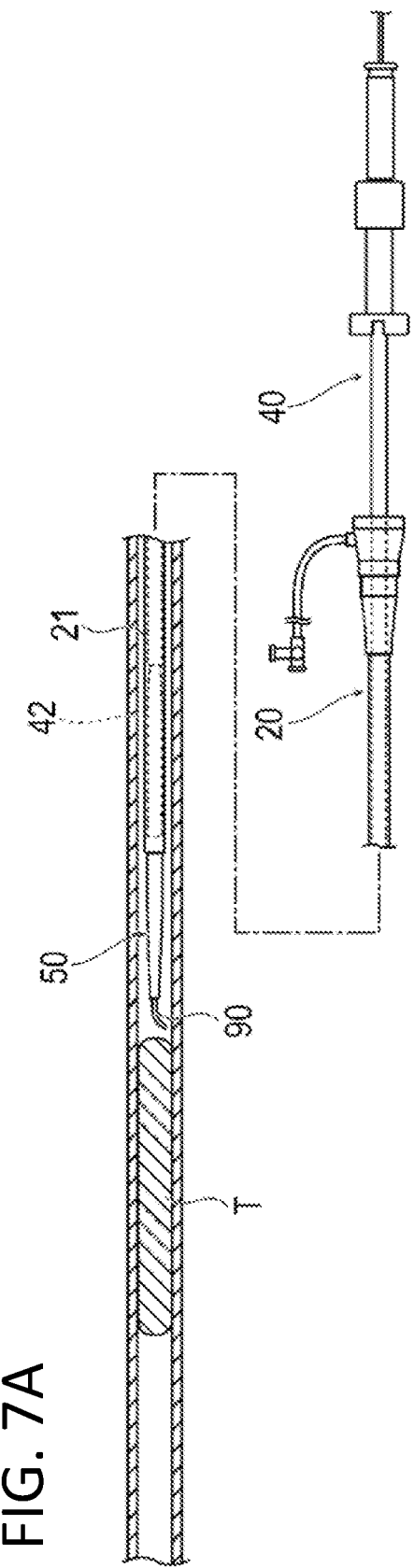

Firstly, an assembly in which the capturing device 40 is accommodated in the outer sheath 20 and the inner sheath 50 is accommodated in the capturing device 40 is prepared as illustrated in FIG. 2A. The capturing portion 42 is deflated inside the outer sheath 20. Accordingly, the hub interlock portion 46 of the hub 43 for capturing is positioned to be closer to the proximal side than the outer sheath hub 22 and is not interlocked with the outer sheath hub 22. The female connector 55 of the inner sheath hub 52 is interlocked with the male connector 47 of the hub 43 for capturing. Next, the iliac artery is punctured with a needle and a guide wire 90 is inserted into the needle. Next, the needle is extracted. Next, the proximal side end portion of the guide wire 90 is inserted inward from the distal side end portion of the inner sheath 50. Next, the above-described assembly is inserted into a blood vessel along the guide wire 90 as illustrated in FIG. 7A.

Figure 7B:
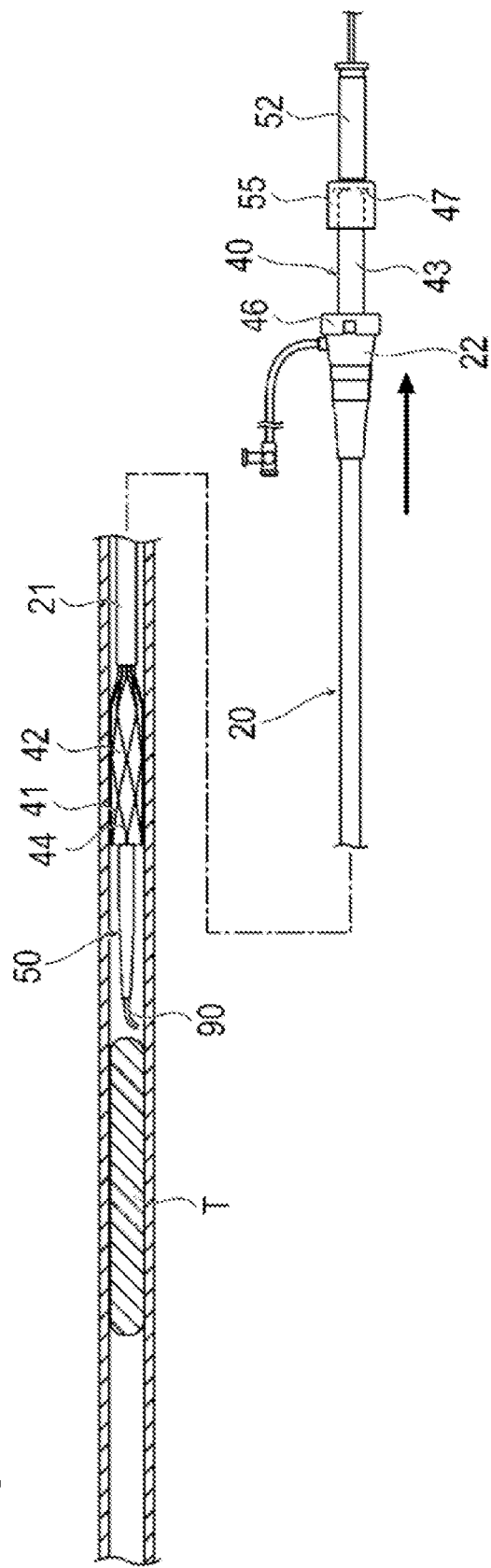

Next, the hub interlock portion 46 is interlocked with the outer sheath hub 22 by the outer sheath 20 being moved to the proximal side with respect to the capturing device 40 as illustrated in FIG. 7B. As a result, the capturing portion 42 is released from the outer sheath main body 21. The capturing portion 42 being released from the outer sheath 20 can be easily grasped by the hub interlock portion 46 being interlocked with the outer sheath hub 22. Once the capturing portion 42 is released from the outer sheath 20, the capturing portion 42 is dilated in the radial direction by the self-expanding force of the elastic portion 44. Accordingly, the outer peripheral surface of the capturing portion 42 comes into close contact with the intravascular wall. The capturing portion 42 is open on the side where the peripheral thrombi T are positioned. As a result, the thrombi T can be drawn into the capturing portion 42.

Next, the inner sheath 50 is extracted from the capturing device 40 as illustrated in FIG. 8A by the female connector 55 of the inner sheath 50 being removed from the male connector 47 of the hub 43 for capturing. Next, the interlock portion 71 of the Y connector 70 is interlocked with the male connector 47 of the hub 43 for capturing as illustrated in FIG. 8B. Subsequently, the distal portion of the medical device 30 is inserted from the main body portion 72 of the Y connector 70. The bent portion 36 of the medical device 30 is substantially linearly stretched and moved inside the sheath 41 for capturing. Once the cutting unit 32 reaches the inside of the capturing portion 42, the bent portion 36 returns to a natural state and is bent as illustrated in FIG. 6B. The cutting unit 32 is capable of rotating in the circumferential direction and is capable of moving along the central axis of the capturing portion 42 inside the capturing portion 42.

Figure 9:
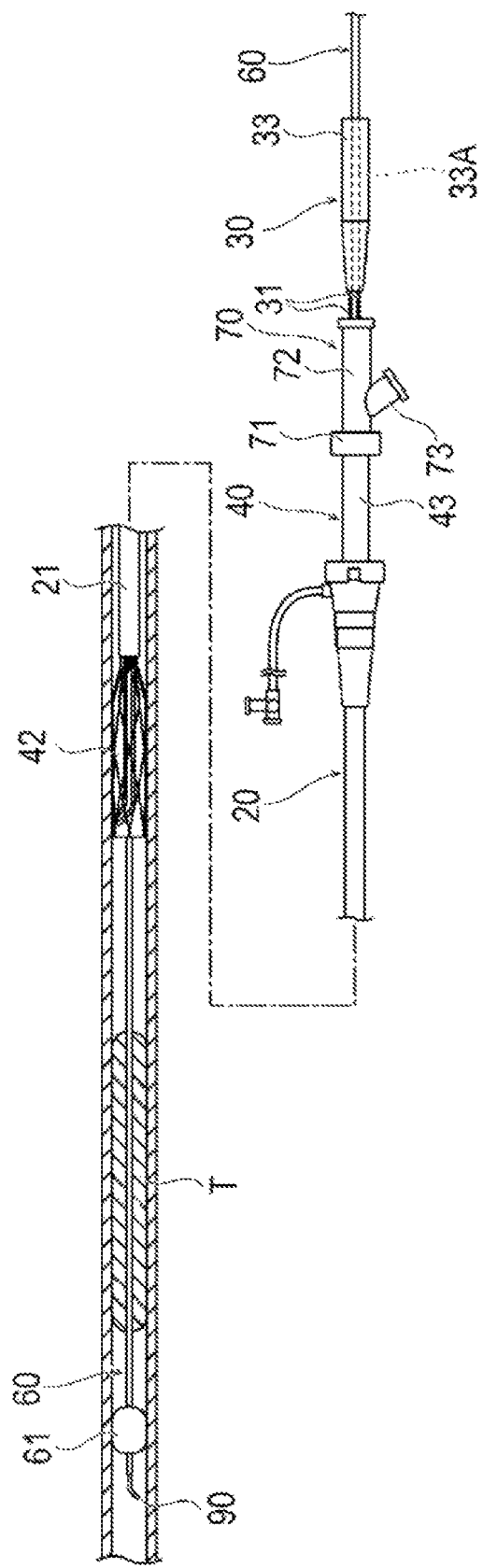
FIG. 9 is a partial sectional view illustrating a state where a thrombus removal device is inserted into a blood vessel.
Figure 10:
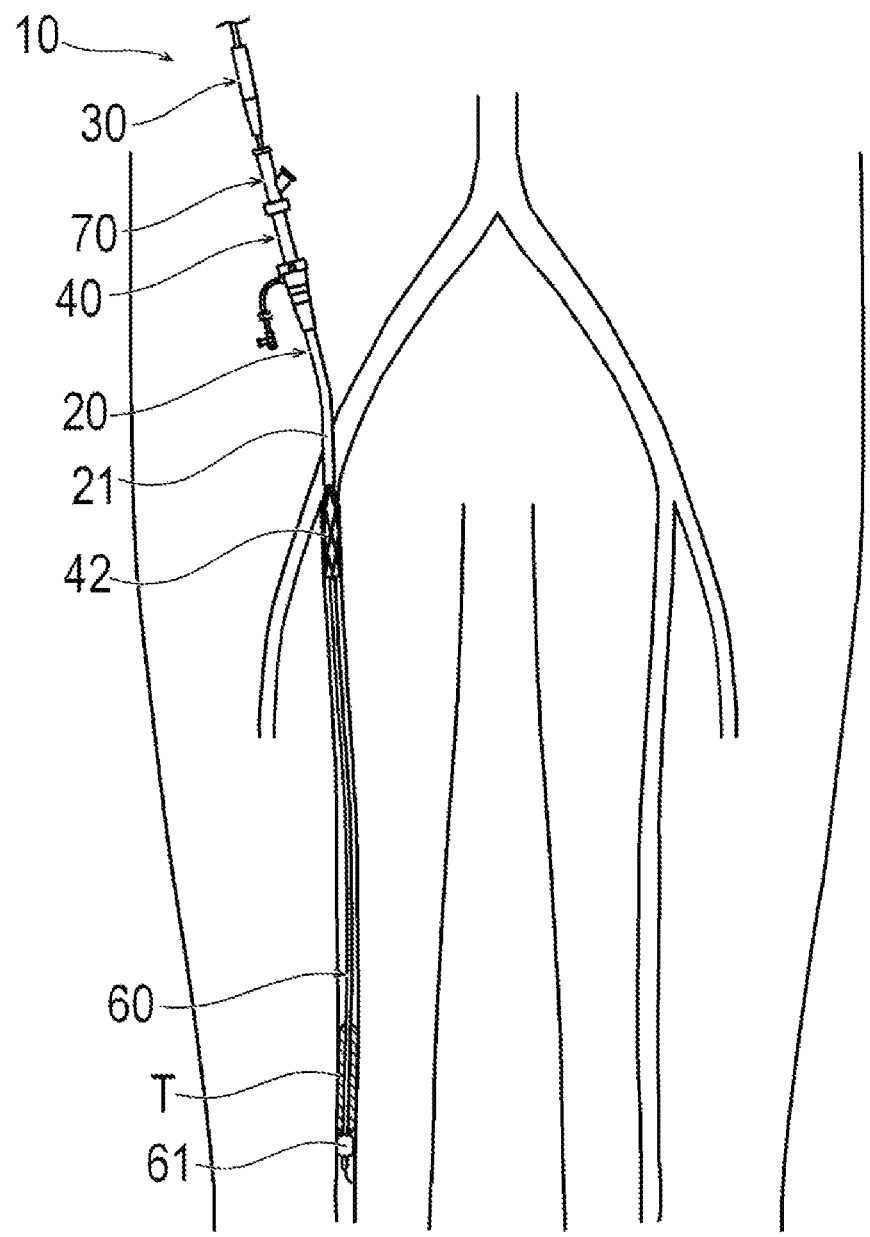
FIG. 10 is a diagram illustrating the state of a blood vessel into which the medical system is inserted.

Next, the thrombus removal device 60 provided with the balloon 61 is inserted into the through-hole 33A from the proximal side of the operation unit 33 by the guide wire 90 being used as a guide. Subsequently, the thrombus removal device 60 is inserted into the capturing device 40 via the Y connector 70. At this time, the thrombus removal device 60 is capable of moving between the two shaft portions 31 since the gap is disposed between the two shaft portions 31 inside the capturing device 40. Subsequently, the thrombus removal device 60 is allowed to reach the distal side of the thrombi T along with the guide wire 90. Subsequently, the balloon 61 is dilated to be capable of moving along the inner peripheral surface of the blood vessel with the vascular lumen blocked as illustrated in FIGS. 9 and 10.

Figure 11:
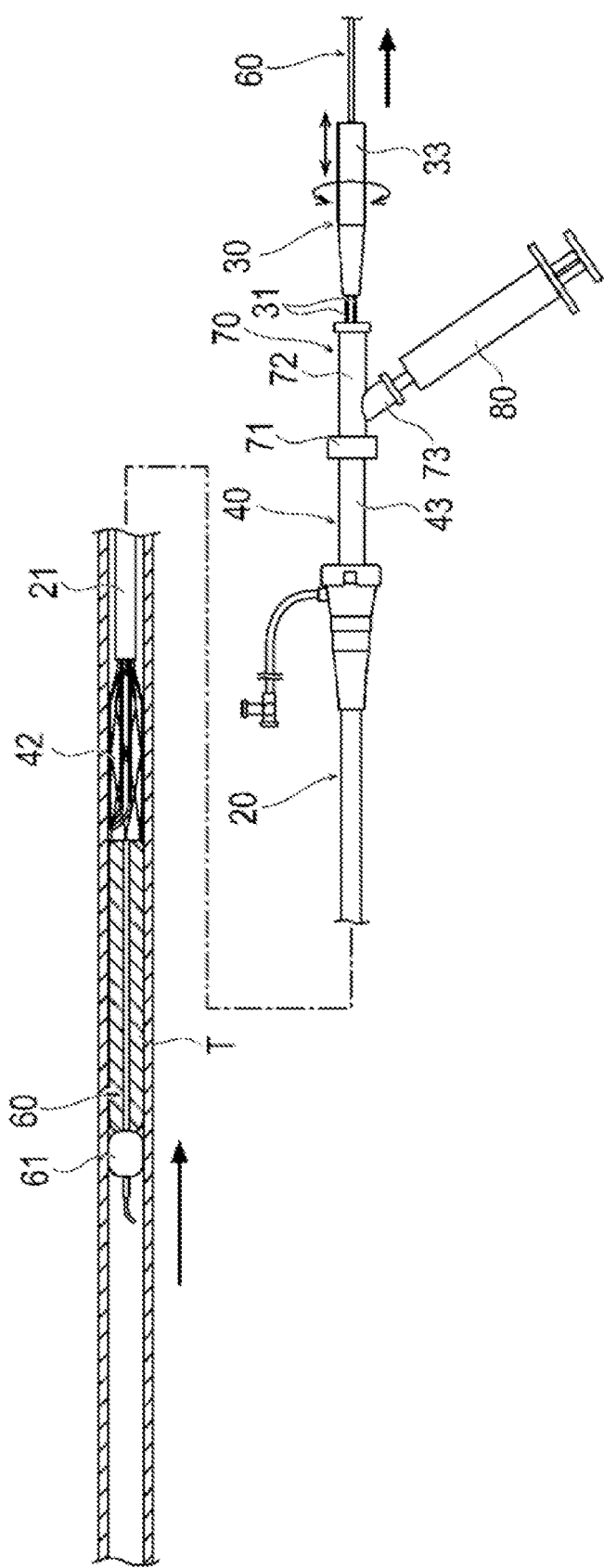
FIG. 11 is a partial sectional view illustrating a state where the thrombus removal device is inserted into a blood vessel.

Next, the balloon 61 is moved to the proximal side in the blood vessel as illustrated in FIGS. 11 and 12A. As a result, the thrombi T are pushed by the balloon 61 and guided into the capturing portion 42. Next, the syringe 80 is interlocked with the side pipe 73 of the Y connector 70 and a thrombolytic agent is supplied from the syringe 80. As a result, the thrombolytic agent is released into the capturing portion 42 and some of the thrombi T are dissolved. Accordingly, the thrombi T can be easily crushed. The thrombolytic agent may not be released into the capturing portion 42, either.

Next, the cutting unit 32 is rotated inside the capturing portion 42 or moved in the axial direction by the operation unit 33 of the medical device 30 being operated. As a result, the thrombi T are finely crushed by the cutting blade 37 of the cutting unit 32. At this time, the cutting unit 32 receives resistance from the thrombi T once the cutting unit 32 is rotated, and thus the cutting unit 32 rotates with a maximum distance smaller than the actual maximum distance L (refer to FIG. 4A). In accordance with an exemplary embodiment, the maximum distance L of the cutting unit 32 is equal to the maximum inner diameter of the capturing portion 42 or exceeds the maximum inner diameter to some extent. Accordingly, the thrombi T positioned close to the inner peripheral surface of the capturing portion 42 can be cut by the cutting unit 32 even when the maximum distance L of the cutting unit 32 decreases. In addition, since no cutting blade 37 is disposed in the distal continuous portion 35, damage to the proximal portion of the balloon 61 and the inner peripheral surface of the capturing portion 42 can be inhibited. Furthermore, the two shaft portions 31 are continuously connected in the distal continuous portion 35 on the distal side and are interlocked in the operation unit 33 on the proximal side. In accordance with an exemplary embodiment, the shaft portion 31 has a relatively short and hard structure. In addition, the position where the capturing portion 42 dilates can be relatively close from the puncture position of the artery, and thus the shaft portion 31 hardly meanders. Accordingly, the two shaft portions 31 integrally rotate with no significant twisting between the distal portion 31A and the proximal portion 31B. Therefore, the two shaft portions 31 interfering with the thrombus removal device 60 passing through the inside thereof can be inhibited. Therefore, tangling between the two shaft portions 31 and the thrombus removal device 60 can be inhibited. In addition, the cutting unit 32 is bent by the bent portion 36, and thus the distal side end portion is unlikely to hit the balloon 61. Therefore, the flat site closer to the proximal side than the distal side end portion of the cutting unit 32 comes into contact with the balloon 61. Therefore, damage to the balloon 61 can be inhibited. In addition, the cutting unit 32 does not protrude to the distal side beyond the capturing portion 42, and thus damage to the blood vessel attributable to the cutting unit 32 can be inhibited and safety is enhanced. Furthermore, since the bending angle β (refer to FIG. 4A) of the bent portion 36 is almost equal to the inclination angle α (refer to FIG. 1) of the proximal side capturing portion 42B, a range that cannot be cut by the cutting unit 32 is unlikely to be formed on the proximal side in the capturing portion 42. Therefore, the thrombi T in the capturing portion 42 can be effectively crushed without exception. Moreover, the thrombi T can be pushed into the capturing portion 42 by the balloon 61, and thus the thrombi T is unlikely to escape during the rotation or movement of the cutting unit 32. Therefore, the thrombi T can be effectively crushed by the cutting unit 32. Moreover, since the blood vessel is blocked by the balloon 61, the thrombolytic agent is maintained with a high concentration around the thrombi T in a case where the thrombolytic agent is injected. Therefore, the effect of the thrombolytic agent can be enhanced. Moreover, the thrombolytic agent is unlikely to move to another site, and thus effects on a living body can be reduced.

Subsequently, the crushed thrombi T are aspirated by the syringe 80 for aspiration being interlocked with the side pipe 73 of the Y connector 70 while the thrombi T are crushed by the cutting unit 32 being rotated and moved in the axial direction as illustrated in FIGS. 11 and 12B. As a result, a negative pressure acts inside the capturing portion 42 via the sheath 41 for capturing. Accordingly, the crushed thrombi T are aspirated by the syringe 80 via the sheath 41 for capturing. At this time, the inner diameter of the proximal side capturing portion 42B decreases toward the proximal side. Therefore, the thrombi T accommodated in the capturing portion 42 can be smoothly guided to the sheath 41 for capturing along the proximal side capturing portion 42B. In a case where the amount of the thrombi T is large and the thrombi T cannot be accommodated in the capturing portion 42 at the same time, the balloon 61 is gradually moved to the proximal side while the thrombi T are crushed, aspirated, and removed. As a result, almost all of the thrombi T can be guided to the capturing portion 42. Once the balloon 61 abuts against the distal side end portion of the capturing portion 42, almost all of the thrombi T are guided into the capturing portion 42 by the balloon 61. The balloon 61 may also be deflated to the point of not coming into close contact with the capturing portion 42 in a case where the aspiration of the thrombi T by the negative pressure is not easy because the balloon 61 touches the inner peripheral surface and the distal side end portion of the capturing portion 42. As a result, blood is allowed to flow from the outside to the inside of the capturing portion 42. Accordingly, the thrombi T in the capturing portion 42 can be aspirated and removed to the syringe 80. Subsequently, almost all of the thrombi T in the capturing portion 42 are removed to the syringe 80 via the sheath 41 for capturing while the thrombi T are crushed by the cutting unit 32 being rotated and moved in the axial direction.

Subsequently, the balloon 61 is deflated and the thrombus removal device 60 is extracted. Subsequently, the medical device 30 is withdrawn from the capturing device 40. At this time, the bent portion 36 is linearly stretched, and the cutting unit 32 is moved from the capturing portion 42 to the sheath 41 for capturing and withdrawn from the hub 43 for capturing.

Figure 13:
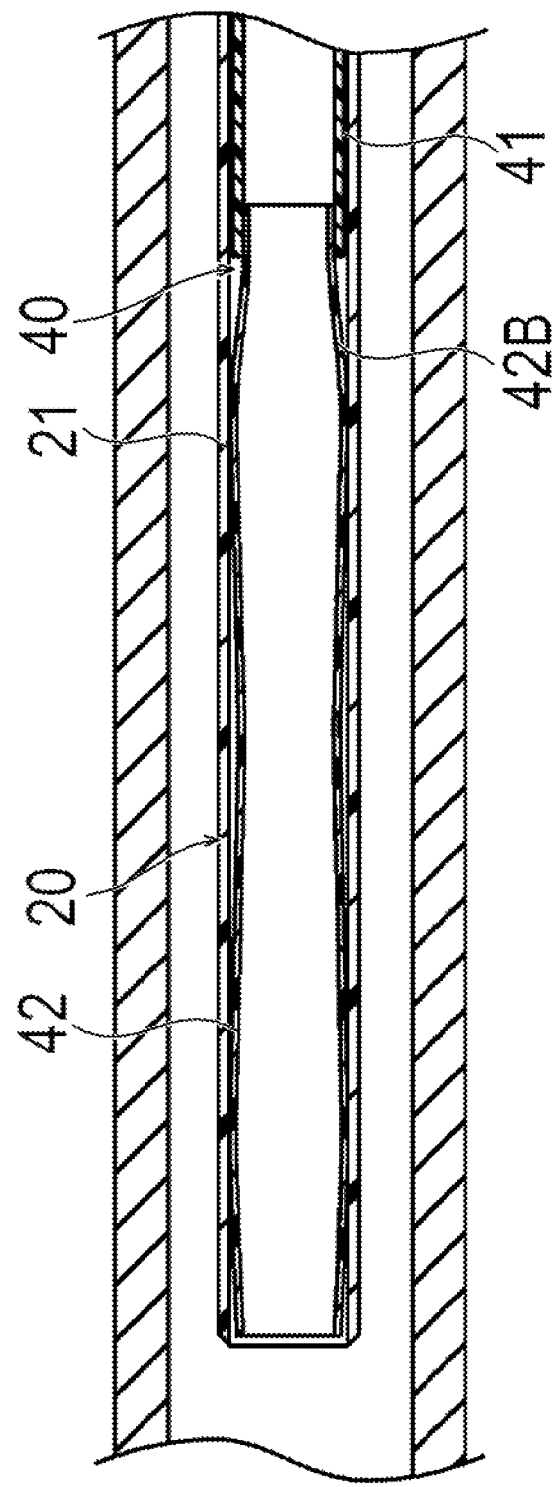
FIG. 13 is a sectional view illustrating a state where the capturing device is accommodated in the outer sheath.

Next, once the outer sheath 20 is relatively moved to the distal side with respect to the capturing device 40, the capturing portion 42 is deflated in the radial direction and accommodated in the outer sheath 20 as illustrated in FIG. 13. At this time, the outer diameter of the proximal side capturing portion 42B decreases toward the proximal side. Accordingly, the capturing portion 42 can be drawn into the outer sheath 20 while the capturing portion 42 is smoothly deflated from the opening portion on the distal side of the outer sheath 20. Subsequently, the outer sheath 20 and the capturing device 40 are extracted from the blood vessel, and the procedure is completed.

As described above, the medical device 30 included in the present embodiment is the medical device 30 that is used after being inserted into the capturing device 40 capturing the thrombi T (object) in a blood vessel (body lumen) and removing the thrombi T to the outside of the body, the medical device 30 has at least two elongated shaft portions 31 spaced apart from each other side by side and extending toward the distal side and the cutting unit 32 extending to the distal side from the distal portions 31A of at least two shaft portions 31, the cutting unit 32 has at least two linear portions 34 inclined with respect to the shaft portions 31 and the distal continuous portion 35 extending to the distal side from the distal portions of at least two linear portions 34, and at least the linear portions 34 have the sharp cutting blades 37.

In the medical device 30 configured as described above, the linear portion 34 provided with the cutting blade 37 is inclined with respect to the shaft portion 31, and thus the thrombi T can be effectively crushed by a movement in the capturing device 40 into which the thrombi T are drawn in the blood vessel. Accordingly, the medical device 30 is capable of effectively crushing the thrombi T inside the capturing device 40 such that the thrombi T are easily removed to the outside of the body. Therefore, the thrombi T can be removed to the outside of the body from the hole in the punctured blood vessel without cutting open the skin even in a case where the thrombi T have a large dimension or a case where the thrombi T are hard. Therefore, invasiveness is relatively low, a patient's physical burden decreases, and the risk of post-treatment infection can be reduced. In addition, no surgical technique as described above is needed since the skin does not have to be cut open. Therefore, a desired effect can be achieved without reliance on an operator's skill. Furthermore, since the blood and the thrombi T inside the capturing portion 42 may be aspirated and removed, excessive aspiration of normal blood can be inhibited. Moreover, the crushed thrombi T are positioned between the capturing portion 42 and the balloon 61, and thus the crushed thrombi T are unlikely to be swept away by a blood flow. Therefore, the risk of peripheral embolism attributable to the crushed thrombi T can be relatively low.

In addition, the cutting blade 37 is positioned to be closer to the proximal side than the most distal portion of the distal continuous portion 35. As a result, damage to the balloon 61 for drawing the thrombi T into the capturing device 40 and the inner peripheral surface of the capturing device 40 into which the thrombi T are drawn can be inhibited.

In addition, the linear portion 34 has the bent portion 36 bent with respect to the central axis of the shaft portion 31 and the cutting blade 37 is positioned to be closer to the distal side than the bent portion 36. As a result, the linear portion 34 can be set to an appropriate angle by the bent portion 36 and damage to the capturing device 40 attributable to the bent portion 36 can be inhibited.

In addition, the linear portion 34 has the two flat surfaces 34C parallel to each other in a cross section perpendicular to the extending direction of the linear portion 34 and the cutting blade 37 is formed in the edge portion of the flat surface 34C. As a result, the cutting blade 37 can be easily formed and a sufficient cutting effect can be achieved.

In addition, the distal continuous portion 35 and the two shaft portions 31 extending from the distal continuous portion 35 are formed of one wire rod. As a result, the number of members can be reduced, and thus manufacturing is facilitated and the occurrence of breakage, for example, can be inhibited by rigidity being maintained at a relatively high level.

In addition, the proximal portions 31B of at least two shaft portions 31 are interlocked with the tubular operation unit 33. As a result, the plurality of shaft portions 31 can be simultaneously operated with the operation unit 33 grasped, and thus operability can be improved. Furthermore, operability can be improved as the thrombus removal device 60 and so on can be inserted by the through-hole 33A in the operation unit 33 being used.

The medical system 10 according to the present embodiment is the medical system 10 inserted into a blood vessel (body lumen) to capture the thrombi T (object) in the blood vessel and remove the thrombi T to the outside of the body, the medical system 10 has the capturing device 40 for capturing the thrombi T in the blood vessel and the medical device 30 inserted into the capturing device 40 to crush the thrombi T captured by the capturing device 40, the medical device 30 has at least two elongated shaft portions 31 spaced apart from each other side by side and extending toward the distal side and the cutting unit 32 extending to the distal side from the distal portions of at least two shaft portions 31, the cutting unit 32 has at least two linear portions 34 inclined with respect to the shaft portions 31 and the distal continuous portion 35 extending to the distal side from the distal portions of at least two linear portions 34, at least the linear portions 34 have the sharp cutting blades 37, the capturing device 40 has the tubular sheath 41 for capturing and the capturing portion 42 that is a pipe body interlocked with the distal portion of the sheath 41 for capturing and communicating with the sheath 41 for capturing and is capable of dilating and deflating in the radial direction, and the cutting unit 32 is capable of moving in the axial direction and the circumferential direction of the capturing portion 42 inside the capturing portion 42.

In the medical system 10 configured as described above, the linear portion 34 provided with the cutting blade 37 is inclined with respect to the shaft portion 31, and thus the thrombi T can be effectively crushed by a movement in the capturing portion 42 into which the thrombi T are drawn in the blood vessel. Accordingly, the medical system 10 is capable of effectively crushing the thrombi T inside the capturing portion 42 and effectively removing the thrombi T to the outside of the body via the sheath 41 for capturing. Therefore, the thrombi T can be removed to the outside of the body from the hole in the punctured blood vessel without cutting open the skin even in a case where the thrombi T have a large dimension or a case where the thrombi T are hard. Therefore, invasiveness can be relatively low, a patient's physical burden decreases, and the risk of post-treatment infection can be reduced. In addition, no surgical technique as described above is needed since the skin does not have to be cut open. Therefore, a desired effect can be achieved without reliance on an operator's skill. Furthermore, since the blood and the thrombi T inside the capturing portion 42 may be aspirated and removed, excessive aspiration of normal blood can be inhibited. Moreover, the crushed thrombi T are positioned between the capturing portion 42 and the balloon 61, and thus the crushed thrombi T are unlikely to be swept away by a blood flow. Therefore, the risk of peripheral embolism attributable to the crushed thrombi T can be relatively low.

In addition, the cutting blade 37 is positioned to be closer to the proximal side than the most distal portion of the distal continuous portion 35. As a result, damage to the balloon 61 for drawing the thrombi T into the capturing portion 42 and the inner peripheral surface of the capturing portion 42 into which the thrombi T are drawn can be inhibited.

In accordance with an exemplary embodiment, the maximum distance L from the central axis of rotation Z of the shaft portion 31 to the site where the cutting unit 32 is farthest away in the direction orthogonal to the central axis of rotation Z is equal to or larger than the maximum inner diameter of the dilated capturing portion 42. As a result, the thrombi T inside the capturing portion 42 can be effectively crushed by the cutting unit 32 rotating inside the capturing portion 42.

The medical system 10 further has the outer sheath 20 capable of accommodating the deflated capturing portion 42. As a result, the deflated capturing portion 42 can be inserted into a blood vessel in a state where the capturing portion 42 is accommodated in the outer sheath 20. Then, the capturing portion 42 can be dilated by being released from the outer sheath 20 at a target position.

In addition, the present disclosure also includes a treatment method (method of treatment) for capturing the thrombi T (object) in a blood vessel (body lumen) and removing the thrombi T to the outside of the body by using the medical system 10 described above. The treatment method includes a step of inserting the capturing device 40 into a blood vessel, a step of dilating the capturing portion 42 in the blood vessel, a step of inserting the distal portion of the thrombus removal device 60 having the balloon 61 (dilation portion) capable of being dilated in the radial direction in the distal portion into the capturing device 40 and allowing the balloon 61 to reach the side closer to the distal side than the thrombi T in the blood vessel, a step of moving the balloon 61 to the proximal side by dilating the balloon 61 and causing the thrombi T to be drawn into the capturing portion 42 by the balloon 61, a step of crushing the thrombi T by moving the cutting unit 32 inside the capturing portion 42, and a step of removing the crushed thrombi T to the outside of the body via the sheath 41 for capturing.

By the treatment method configured as described above, the thrombi T can be effectively crushed by the cutting unit 32 inclined with respect to the shaft portion 31 provided with the cutting blade 37 being moved in the capturing portion 42 into which the thrombi T are drawn in the blood vessel. In addition, since the cutting unit 32 is positioned to be closer to the proximal side than the most distal portion of the distal continuous portion 35, damage to the balloon 61 for drawing the thrombi T into the capturing portion 42 and the inner peripheral surface of the capturing portion 42 into which the thrombi T are drawn can be inhibited. Accordingly, by the treatment method, damage to the instruments that are used together can be reduced and the thrombi T inside the capturing portion 42 can be effectively crushed and effectively removed to the outside of the body via the sheath 41 for capturing. Therefore, the thrombi T can be removed to the outside of the body from the hole in the punctured blood vessel without cutting open the skin even in a case where the thrombi T have a large dimension or a case where the thrombi T are hard. Therefore, invasiveness can be relatively low, a patient's physical burden decreases, and the risk of post-treatment infection can be reduced. In addition, no surgical technique as described above is needed since the skin does not have to be cut open. Therefore, a desired effect can be achieved without reliance on an operator's skill. Furthermore, since the blood and the thrombi T inside the capturing portion 42 may be aspirated and removed, excessive aspiration of normal blood can be inhibited. Moreover, the crushed thrombi T are positioned between the capturing portion 42 and the balloon 61, and thus the crushed thrombi T are unlikely to be swept away by a blood flow. Therefore, the risk of peripheral embolism attributable to the crushed thrombi T can be relatively low.

The present disclosure is not limited to the embodiment described above, and various modifications are possible by those skilled in the art within the technical scope of the present disclosure. For example, the object to be removed is not limited to thrombi and can also be any object that can be present in a body lumen such as plaque and a calcified lesion. The body lumen is not limited to a blood vessel and may also be, for example, a vessel, a ureter, a bile duct, a fallopian tube, or a hepatic duct.

Figure 14:
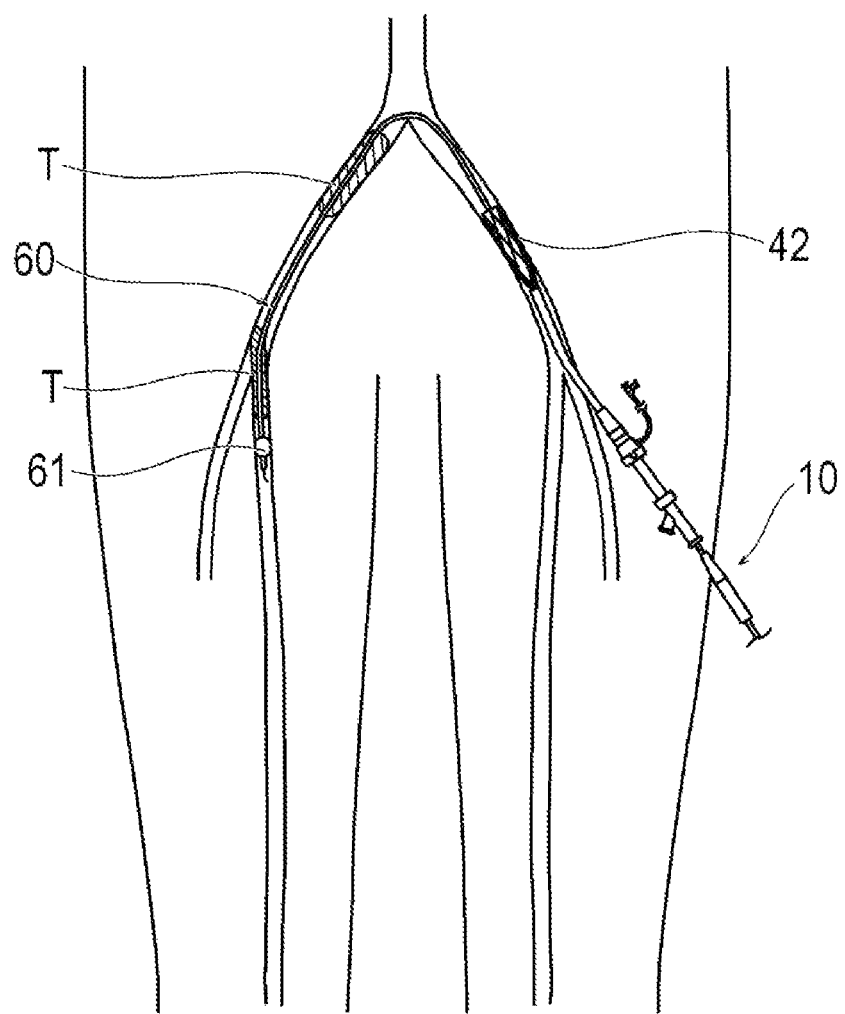
FIG. 14 is a diagram illustrating the state of a blood vessel into which the medical system is inserted.

The medical system 10 may also be inserted from an iliac artery on the opposite side as illustrated in FIG. 14 so that the thrombi T obstructing the iliac artery are removed by the medical system 10 described above. In this case, the opening portion of the capturing portion 42 is directed toward the heart. As a result, the thrombus removal device 60 is allowed to undergo crossover approach to the iliac artery on the opposite side.

Figure 15:
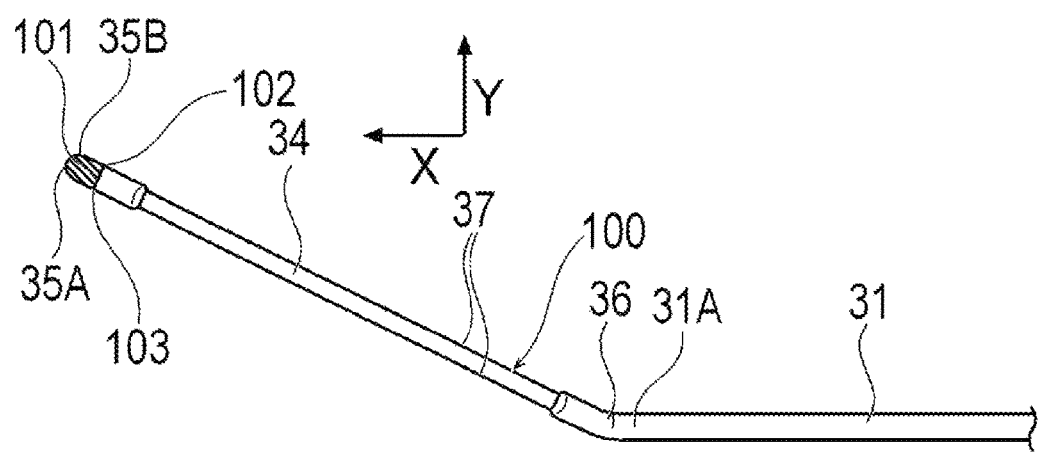
FIG. 15 is a sectional view illustrating a first modification example of the medical device.

In addition, a cutting blade 102 may be formed on the surface of a distal continuous portion 101 of a cutting unit 100 on the side opposite to the distal direction X and a cutting blade 103 may be formed on the surface of the distal continuous portion 101 on the side opposite to the separation direction Y as in a first modification example illustrated in FIG. 15. The same reference numerals will be used to refer to the sites that have the same functions as in the embodiment described above, and description thereof will be omitted. As in the embodiment described above, no cutting blade is formed on the tip surface 35A of the distal continuous portion 101 on the distal direction X side and the side surface 35B on the separation direction Y side. Damage to the balloon 61 and the inner peripheral surface of the capturing portion 42 can be inhibited with this configuration as well.

Figure 16:
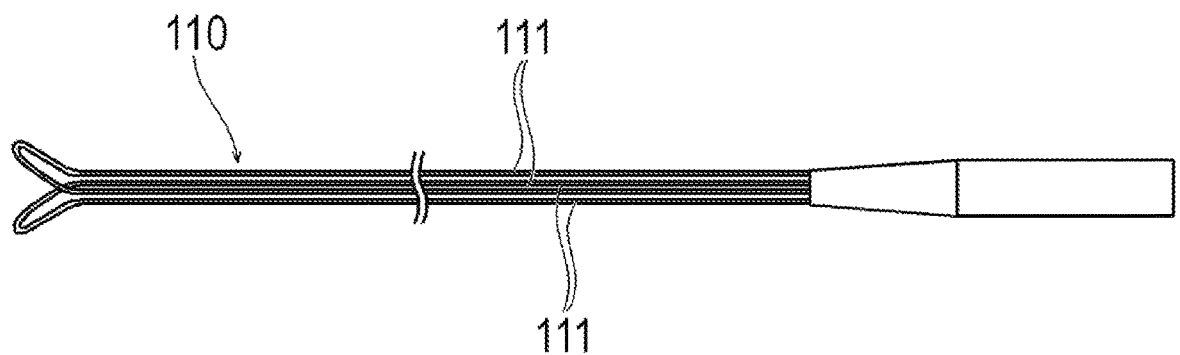
FIG. 16 is a plan view illustrating a second modification example of the medical device.

In addition, a medical device 110 may be provided with three or more (for example, four in FIG. 16) shaft portions 111 as in a second modification example illustrated in FIG. 16. In accordance with an exemplary embodiment, cuttablity may be improved with this configuration.

Figure 17:
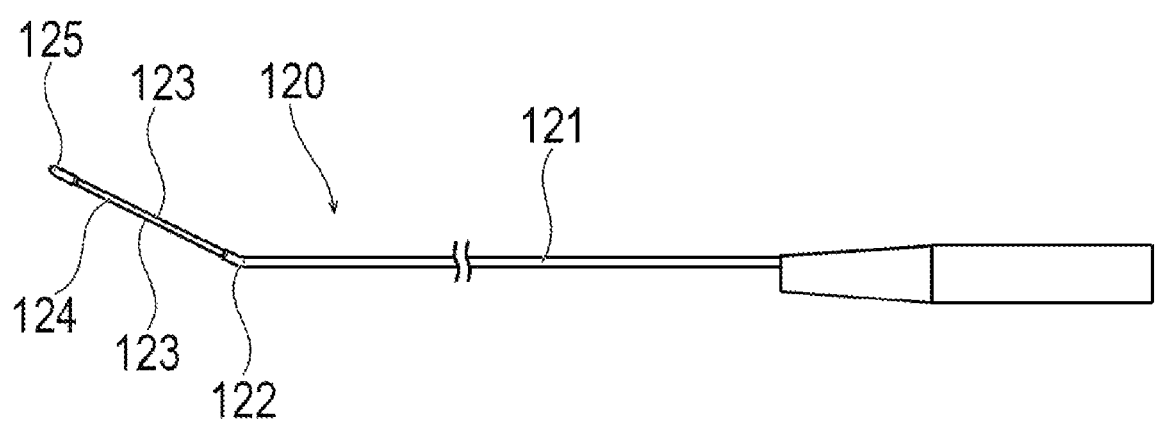
FIG. 17 is a sectional view illustrating a third modification example of the medical device.

In addition, a medical device 120 may have one shaft portion 121 as in a third modification example illustrated in FIG. 17. A cutting unit 124 provided with a bent portion 122 and a cutting blade 123 is disposed on the distal side of the shaft portion 121. A distal side end portion 125 of the cutting unit 124 has no cutting blade and has a smooth outer surface.

In addition, the cutting unit of the medical device may be inserted into a blood vessel along with the capturing device in a state where the cutting unit is accommodated in the capturing device. In addition, the medical device may be provided with a structure rotated by a motor or the like.

In addition, the configuration of the thrombus removal device is not particularly limited. For example, the thrombus removal device may have a dilation portion dilated in the radial direction by an elastic body that has a self-expanding force instead of the balloon dilated by a fluid.

The detailed description above describes a medical device, a medical system, and a treatment method for removing thrombi in a blood vessel. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment method for capturing an object in a body lumen and removing the object to an outside of a body by using a removal device including a dilation portion configured to be dilated in a radial direction in a distal portion, a capturing device including a capturing portion and a sheath configured to remove the captured object in a tip portion configured to capture the object in the body lumen, and a cutting device including a cutting unit configured to crush the object captured by the capturing device, the cutting device including a bent portion, and before crushing the object captured by the capturing device, positioning a distal continuous portion of the cutting device with respect to an inner surface of the capturing device to prevent the cutting device from damaging the dilation portion, the treatment method comprising:

inserting the capturing device into the body lumen;
dilating the capturing portion in the body lumen;
inserting the distal portion of the removal device into the capturing device and allowing the dilation portion to reach a side closer to a distal side than the object in the body lumen;
moving the dilation portion to a proximal side by dilating the dilation portion and causing the object to be drawn into the capturing portion by the dilation portion and then abutting the dilation portion against a distal side end portion of the capturing portion to occlude the distal side end portion of the capturing portion;
crushing the object by rotating the cutting unit inside the occluded capturing portion; and
removing the crushed object to the outside of the body via the sheath for capturing.

2. The method according to claim 1, further comprising:
moving the cutting unit in an axial direction inside the occluded capturing portion.

3. The method according to claim 1, wherein the capturing device has a tubular sheath configured to capture the object and the capturing portion is a tubular body interlocked with a distal portion of the sheath, the method further comprising:
dilating the capturing portion in the body lumen in a radial direction.

4. The method according to claim 3, comprising:
contracting the capturing portion after the removal of the crushed object to the outside of the body via the sheath.

5. The method according to claim 4, comprising:
accommodating the capturing portion in a deflated state in a tubular outer sheath.

6. The method according to claim 1, comprising:
removing the crushed object to the outside of the body via the sheath by aspiration using a syringe.

7. The method according to claim 1, wherein an inner diameter of a proximal portion of the capturing portion decreases toward a proximal side, and the method further comprises:
applying a negative pressure inside the capturing portion to guide the crushed object into the sheath.

8. The method according to claim 1, wherein the cutting unit has at least two linear portions inclined and the distal continuous portion extending to the distal side from distal portions of the at least two linear portions, and wherein at least the at least two linear portions have cutting blades.

9. A treatment method for capturing an object in a body lumen and removing the object to an outside of a body by using a removal device including a dilation portion configured to be dilated in a radial direction in a distal portion, a capturing device including a capturing portion and a sheath configured to remove the captured object in a tip portion configured to capture the object in the body lumen, and a cutting device including a cutting unit configured to crush the object captured by the capturing device, the cutting device including a bent portion, and before crushing the object captured by the capturing device, positioning a distal continuous portion of the cutting device with respect to an inner surface of the capturing device to prevent the cutting device from damaging the dilation portion, the treatment method comprising:

inserting the capturing device into the body lumen;
dilating the capturing portion in the body lumen;
inserting the distal portion of the removal device into the capturing device and allowing the dilation portion to reach a side closer to a distal side than the object in the body lumen;
moving the dilation portion to a proximal side by dilating the dilation portion and causing the object to be drawn into the capturing portion by the dilation portion then abutting the dilation portion against a distal side end portion of the capturing portion to occlude the distal side end portion of the capturing portion;
crushing the object by rotating the cutting unit inside the occluded capturing portion; and
removing the crushed object to the outside of the body via the sheath for capturing.

10. The method according to claim 9, wherein the capturing device has a tubular sheath configured to capture the object and the capturing portion is a tubular body interlocked with a distal portion of the sheath, the method further comprising:
dilating the capturing portion in the body lumen in a radial direction.

11. The method according to claim 10, comprising:
contracting the capturing portion after the removal of the crushed object to the outside of the body via the sheath.

12. The method according to claim 11, comprising:
accommodating the capturing portion in a deflated state in a tubular outer sheath.

13. The method according to claim 9, comprising:
removing the crushed object to the outside of the body via the sheath by aspiration using a syringe.

14. The method according to claim 9, wherein an inner diameter of a proximal portion of the capturing portion decreases toward a proximal side, and the method further comprises:
applying a negative pressure inside the capturing portion to guide the crushed object into the sheath.

15. The method according to claim 9, wherein the cutting unit has at least two linear portions inclined and the distal continuous portion extending to the distal side from distal portions of the at least two linear portions, and wherein at least the at least two linear portions have cutting blades.

16. The method according to claim 9, wherein the crushing of the object further comprises:
moving the cutting unit in an axial direction inside the occluded capturing portion.

17. The method according to claim 1, wherein the cutting device has a cutting blade between the distal continuous portion and the bent portion and the distal continuous portion is not sharp.

18. The method according to claim 17, wherein the cutting blade is positioned closer to the bent portion than the distal continuous portion.

19. The method according to claim 18, wherein the distal continuous portion has a circular shape, an elliptical shape, or a distorted circular shape, and the cutting blade is flat.

* * * * *